(12) United States Patent
Alenfall et al.

(10) Patent No.: US 10,815,283 B2
(45) Date of Patent: Oct. 27, 2020

(54) PEPTIDES FOR TREATMENT OF DIABETES

(71) Applicant: Follicum AB, Lund (SE)

(72) Inventors: Jan Alenfall, Lomma (SE); Pontus Dunér, Dalby (SE); Anna Hultgårdh Nilsson, Genarp (SE); Björn Walse, Lund (SE)

(73) Assignee: Follicum AB, Lund (SE)

( * ) Notice: Subject to any disclaimer, the term of this patent is extended or adjusted under 35 U.S.C. 154(b) by 0 days.

(21) Appl. No.: 16/666,960

(22) Filed: Oct. 29, 2019

(65) Prior Publication Data
US 2020/0095297 A1    Mar. 26, 2020

Related U.S. Application Data

(63) Continuation of application No. PCT/EP2018/061547, filed on May 4, 2018.

(30) Foreign Application Priority Data

May 4, 2017    (EP) .................................... 17169500

(51) Int. Cl.
| | | |
|---|---|---|
| C07K 14/47 | (2006.01) | |
| A61P 3/10 | (2006.01) | |
| A61K 38/16 | (2006.01) | |
| A61K 38/17 | (2006.01) | |
| A61K 38/45 | (2006.01) | |
| A61K 45/06 | (2006.01) | |
| C07K 14/00 | (2006.01) | |
| C07K 14/31 | (2006.01) | |
| C12N 9/10 | (2006.01) | |

(52) U.S. Cl.
CPC ........ *C07K 14/4705* (2013.01); *A61K 38/164* (2013.01); *A61K 38/1709* (2013.01); *A61K 38/45* (2013.01); *A61K 45/06* (2013.01); *A61P 3/10* (2018.01); *C07K 14/001* (2013.01); *C07K 14/31* (2013.01); *C12N 9/1088* (2013.01); *C12Y 205/01018* (2013.01); *C07K 2319/00* (2013.01); *C07K 2319/40* (2013.01)

(58) Field of Classification Search
None
See application file for complete search history.

(56) References Cited

U.S. PATENT DOCUMENTS

| | | |
|---|---|---|
| 6,482,410 B1 | 11/2002 | Crossin et al. |
| 7,662,633 B2 | 2/2010 | Barry et al. |
| 2010/0150877 A1 | 6/2010 | O'Brien et al. |
| 2016/0317620 A1 | 11/2016 | Alenfall et al. |

FOREIGN PATENT DOCUMENTS

| | | |
|---|---|---|
| WO | WO-9608513 A1 * | 3/1996 ............ C07K 14/47 |
| WO | 9915904 A1 | 4/1999 |
| WO | 0033865 A1 | 6/2000 |
| WO | 200171358 A1 | 9/2001 |
| WO | 200196395 A2 | 12/2001 |
| WO | 2002092122 A2 | 11/2002 |
| WO | 2003006893 A2 | 1/2003 |
| WO | 2003100007 A2 | 12/2003 |
| WO | 2008086449 A2 | 7/2008 |
| WO | 2008107422 A1 | 9/2008 |
| WO | 2008128456 A1 | 10/2008 |
| WO | 2008131094 A1 | 10/2008 |
| WO | 2009058379 A2 | 5/2009 |
| WO | 2011058182 A1 | 5/2011 |
| WO | 2013021212 A3 | 2/2013 |
| WO | 2014013060 A1 | 1/2014 |
| WO | 2015159099 A1 | 10/2015 |
| WO | 2017192820 A1 | 11/2017 |

OTHER PUBLICATIONS

Kinoshita et al. ("Distinct Glycosylation in Interstitial and Serum Tenascin-X," Biol. Pharm. Bull. 30(2) 354-358 (2007)) (Year: 2007).*
Valcourt et al. ("Tenascin-X: beyond the architectural function," Cell Adhesion & Migration 9:1-2, 154-165; Jan.-Apr. 2015) (Year: 2015).*
Miller et al. ("Genetic diversity and population structure of the endangered marsupial *Sarcophilus harrisii* (Tasmanian devil)" Proc. Natl. Acad. Sci. U.S.A. 108:12348-12353(2011) (Year: 2011).*
UniProt entry G3W6G8_SARHA, downloaded May 9, 2020 (Year: 2020).*
Chapman et al; "Osteopontin is required for the early onset of high fat diet-induced insulin resistance in mice". PLoS One 5(11):e13959. Year: 2010.
Gong et al; "Expression and regulation of osteopontin in type 1 diabetes". (2009) Islets 1(1):34-4. Year: 2009.
Gopal et al; "Association of Salivary Osteopontin Levels with Glycaemic Status and Microalbuminuria—in Patients with Type 2 Diabetes Mellitus". (2016) J Clin Diagn Res. 10(8):BC06-8. Year: 2016.
Kiefer et al; "Neutralization of osteopontin inhibits obesity-induced inflammation and insulin resistance". (Apr. 2010) Diabetes, vol. 59, pp. 935-946. Year:2010.
Sarosiek et al; "Osteopontin (OPN) Isoformas, Diabetes, Ibesity, and Cencer; What Is One Got to Do with the Other? A New Role for OPN". Journal of gastrointestinal Surgery, Quality Medical Publ., St. Louis, MO, US, vol. 19 , No. 4, Jan. 13, 2015, pp. 639-650. Year: 2015.

* cited by examiner

*Primary Examiner* — Christina Bradley
(74) *Attorney, Agent, or Firm* — Dinsmore & Shohl LLP; Weston R. Gould

(57) ABSTRACT

The present disclosure concerns agents and their use in the treatment of endocrine, nutritional and/or metabolic diseases in a mammal. The disclosure furthermore concerns novel peptides.

24 Claims, 18 Drawing Sheets
Specification includes a Sequence Listing.

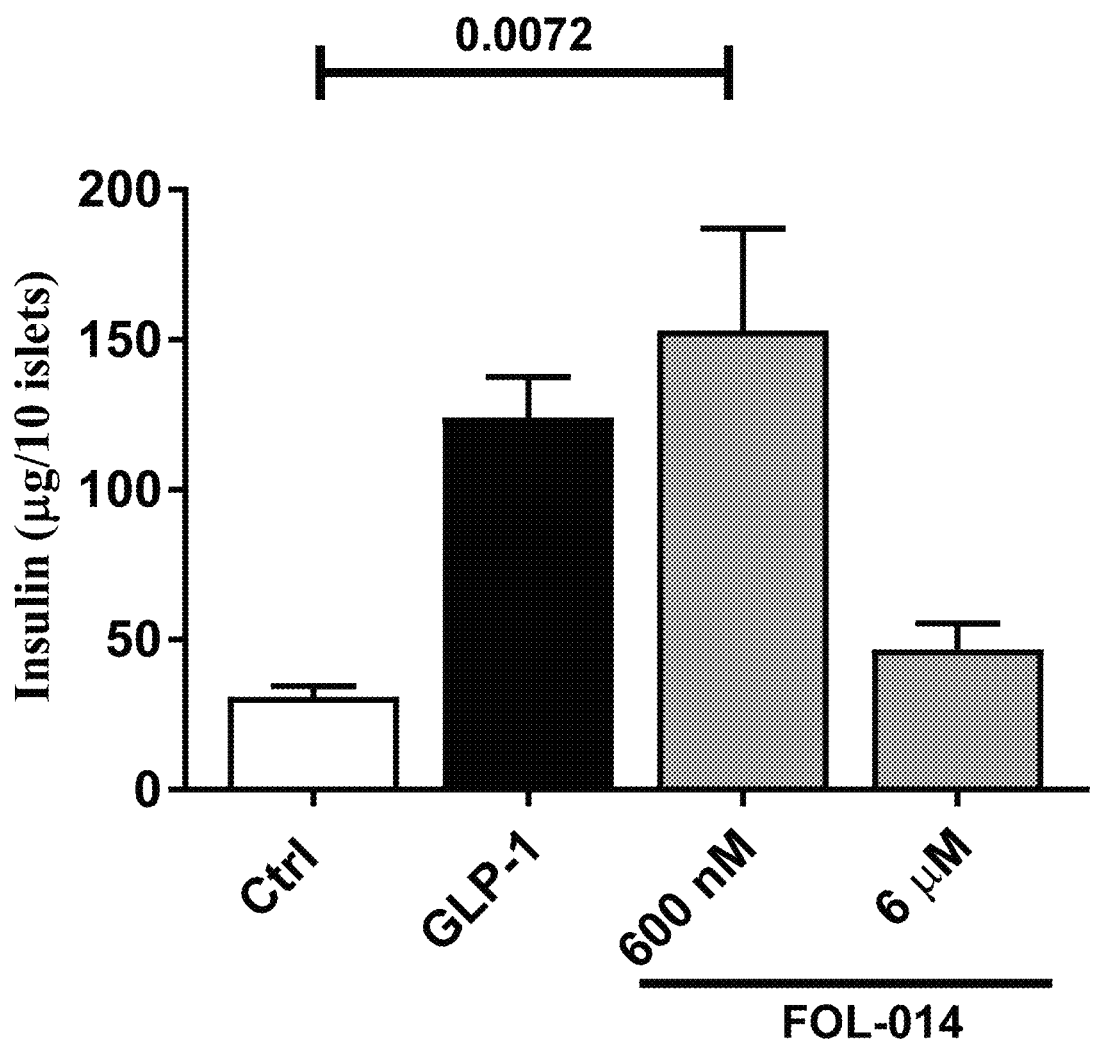
Fig. 8, cont.

Fig. 8, cont.
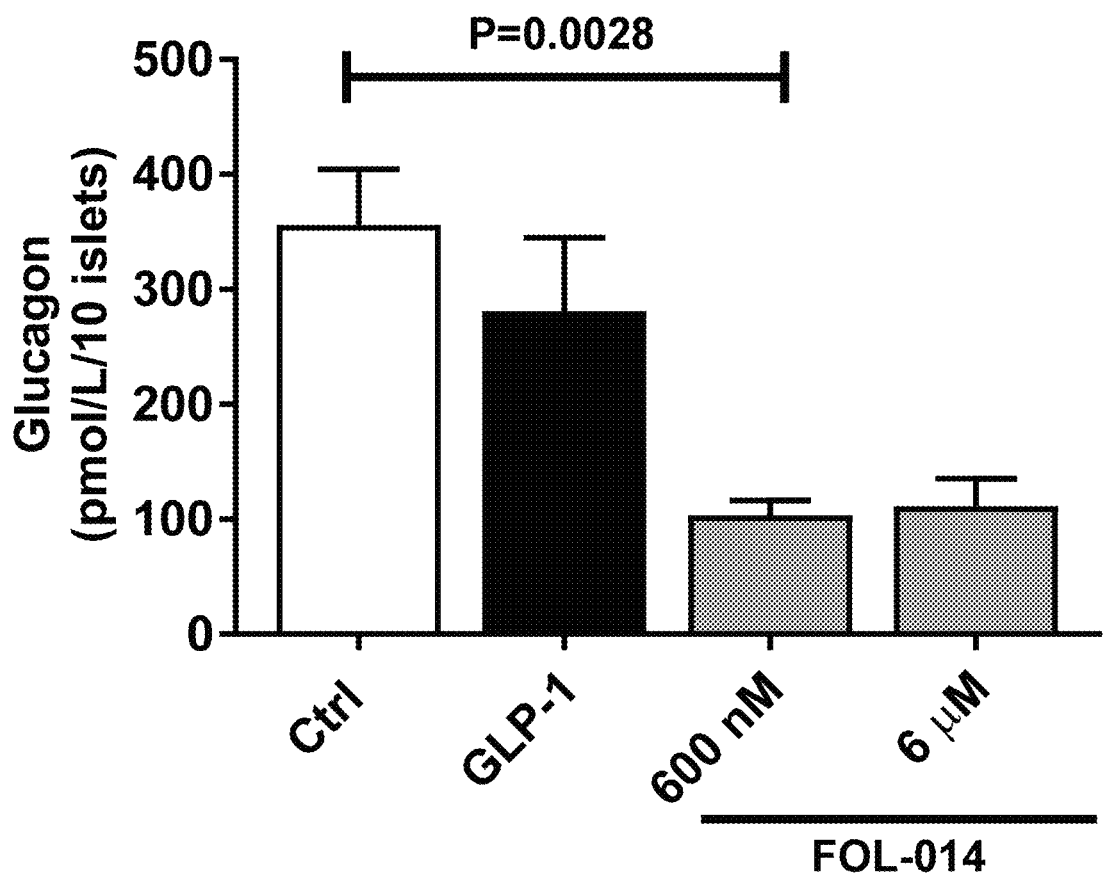

Fig. 8, cont.
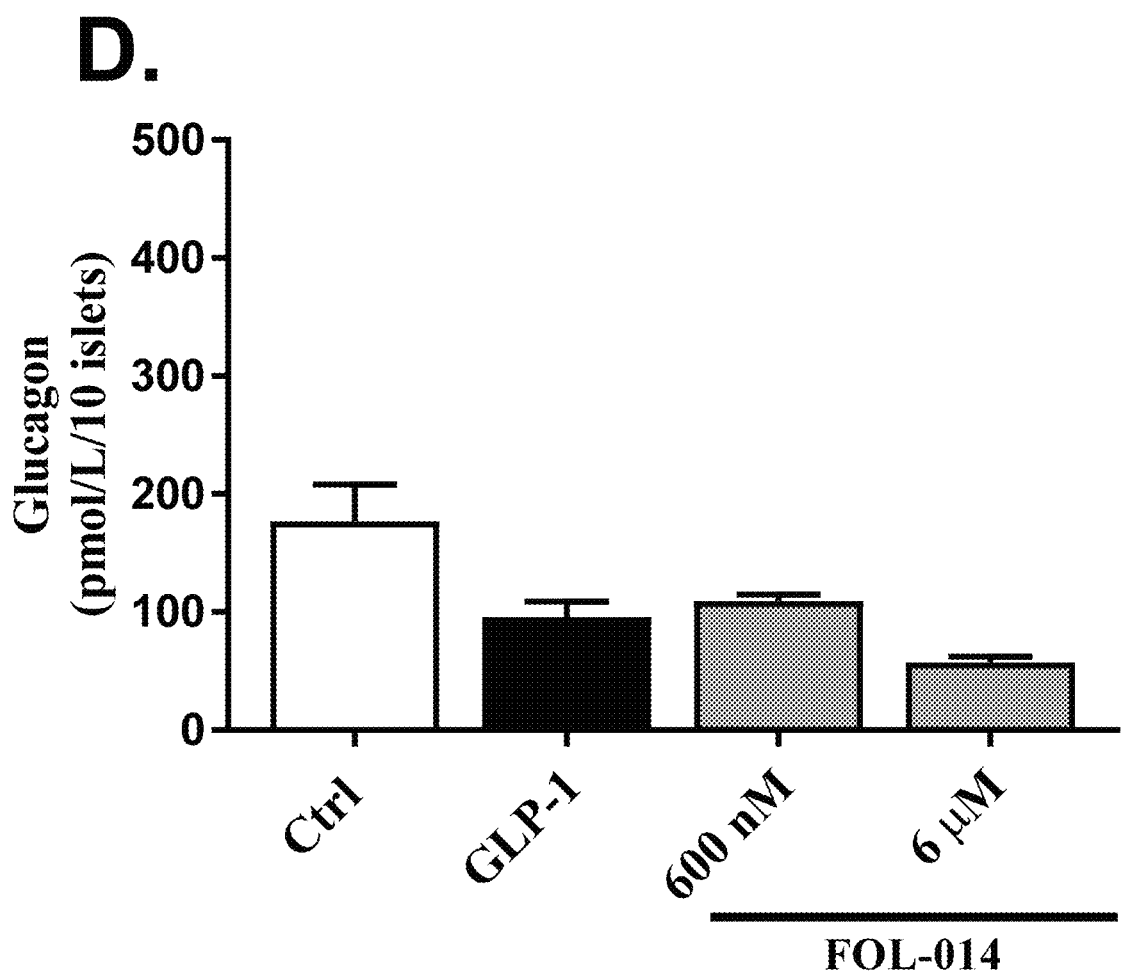

Fig. 9, cont.
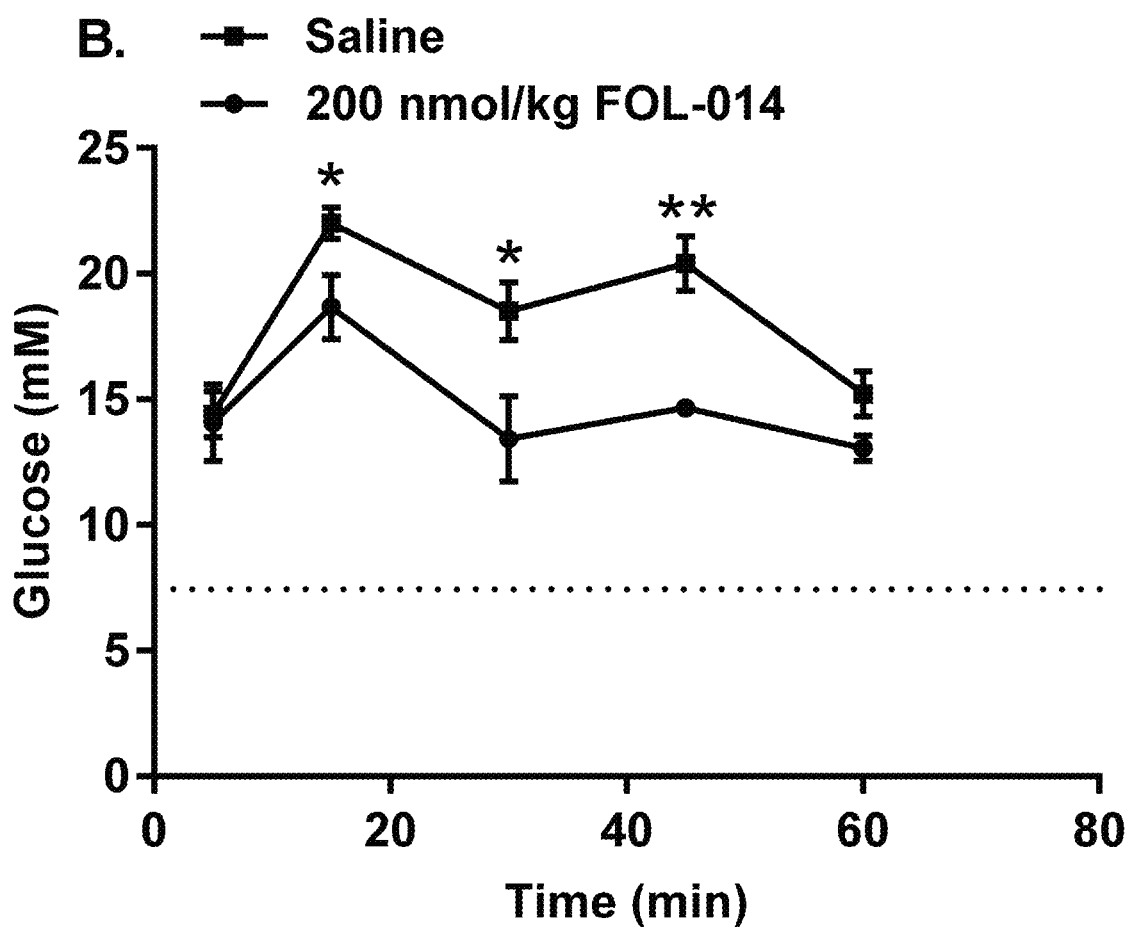

Fig. 10, cont.
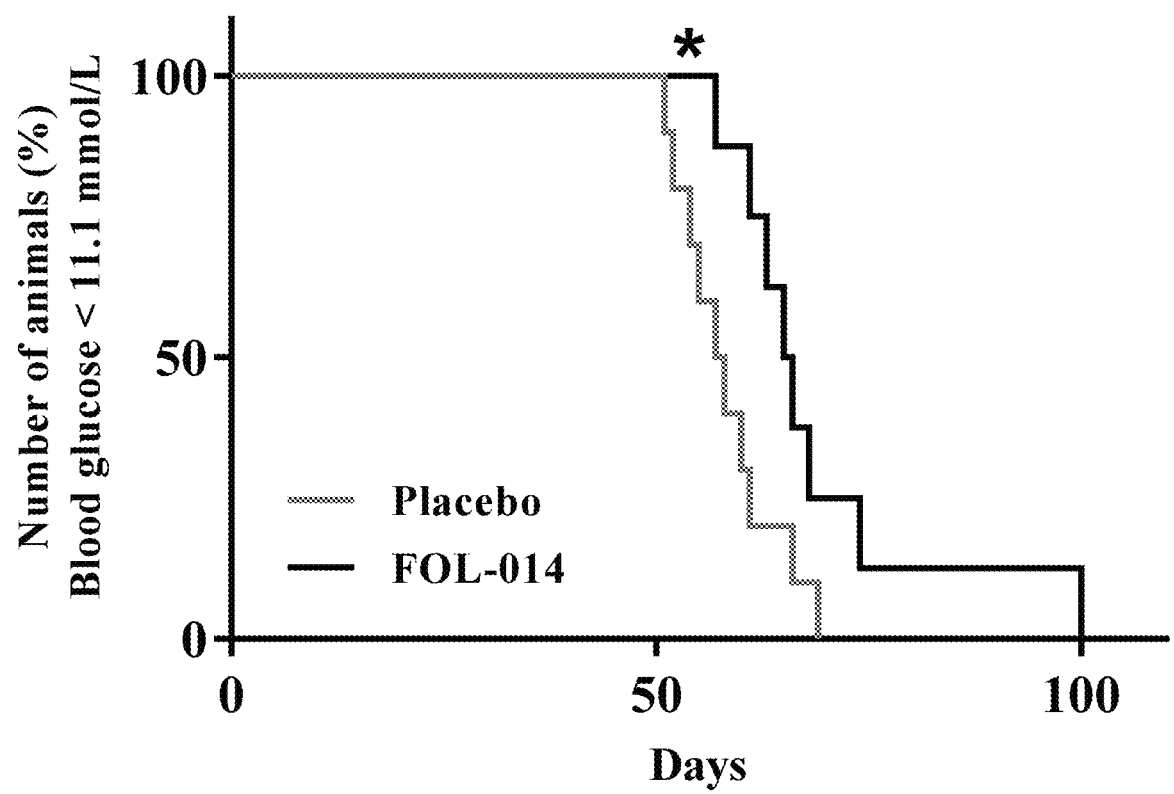

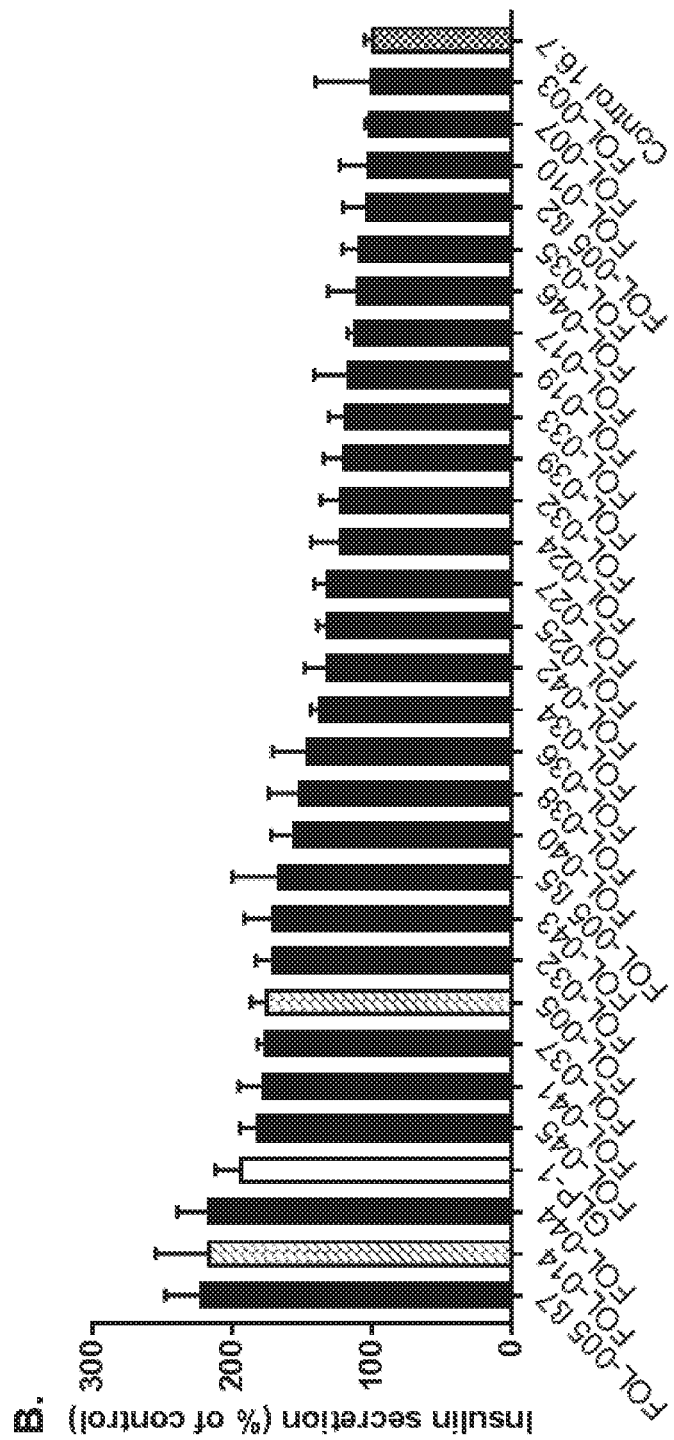
Fig. 11, cont.

A

B

C

D

SEQUENCE LISTING

<160> NUMBER OF SEQ ID NOS: 169

<210> SEQ ID NO 1
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide, FOL-005

<400> SEQUENCE: 1

Val Asp Thr Tyr Asp Gly Asp Ile Ser Val Val Tyr Gly Leu Arg
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide

<400> SEQUENCE: 2

Val Asp Thr Tyr Asp Gly Asp Ile Ser Val Val Tyr Gly Leu Ser
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(14)
<223> OTHER INFORMATION: peptide, FOL-025

<400> SEQUENCE: 3

Val Asp Thr Tyr Asp Gly Asp Ile Ser Val Val Tyr Gly Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(14)
<223> OTHER INFORMATION: peptide

<400> SEQUENCE: 4

Asp Thr Tyr Asp Gly Asp Ile Ser Val Val Tyr Gly Leu Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic sequence

```
<220> FEATURE:
<221> NAME/KEY: MISC_FEATURE
<222> LOCATION: (1)..(14)
<223> OTHER INFORMATION: peptide

<400> SEQUENCE: 5

Thr Tyr Asp Gly Asp Ile Ser Val Val Tyr Gly Leu Arg Ser
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide, FOL-024

<400> SEQUENCE: 6

Val Asp Thr Tyr Asp Gly Asp Ile Ser Val Val Tyr Gly
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 7

Asp Thr Tyr Asp Gly Asp Ile Ser Val Val Tyr Gly Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 8

Thr Tyr Asp Gly Asp Ile Ser Val Val Tyr Gly Leu Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 9

Tyr Asp Gly Asp Ile Ser Val Val Tyr Gly Leu Arg Ser
1               5                   10
```

```
<210> SEQ ID NO 10
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 10

Val Asp Thr Tyr Asp Gly Asp Ile Ser Val Val Tyr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 11

Asp Thr Tyr Asp Gly Asp Ile Ser Val Val Tyr Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 12

Thr Tyr Asp Gly Asp Ile Ser Val Val Tyr Gly Leu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 13

Tyr Asp Gly Asp Ile Ser Val Val Tyr Gly Leu Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide
```

```
<400> SEQUENCE: 14

Asp Gly Asp Ile Ser Val Val Tyr Gly Leu Arg Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 15

Val Asp Thr Tyr Asp Gly Asp Ile Ser Val Val
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 16

Asp Thr Tyr Asp Gly Asp Ile Ser Val Val Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 17

Thr Tyr Asp Gly Asp Ile Ser Val Val Tyr Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 18

Tyr Asp Gly Asp Ile Ser Val Val Tyr Gly Leu
1               5                   10

<210> SEQ ID NO 19
<211> LENGTH: 11
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 19

Asp Gly Asp Ile Ser Val Val Tyr Gly Leu Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 20

Gly Asp Ile Ser Val Val Tyr Gly Leu Arg Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 21

Val Asp Thr Tyr Asp Gly Asp Ile Ser Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 22

Asp Thr Tyr Asp Gly Asp Ile Ser Val Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 23

Thr Tyr Asp Gly Asp Ile Ser Val Val Tyr
1               5                   10
```

-continued

```
<210> SEQ ID NO 24
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 24

Tyr Asp Gly Asp Ile Ser Val Val Tyr Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 25

Asp Gly Asp Ile Ser Val Val Tyr Gly Leu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide, FOL-009h

<400> SEQUENCE: 26

Gly Asp Ile Ser Val Val Tyr Gly Leu Arg
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 27

Asp Ile Ser Val Val Tyr Gly Leu Arg Ser
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide, FOL-019h
```

```
<400> SEQUENCE: 28

Val Asp Thr Tyr Asp Gly Asp Ile Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 29

Asp Thr Tyr Asp Gly Asp Ile Ser Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 30

Thr Tyr Asp Gly Asp Ile Ser Val Val
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 31

Tyr Asp Gly Asp Ile Ser Val Val Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 32

Asp Gly Asp Ile Ser Val Val Tyr Gly
1               5

<210> SEQ ID NO 33
<211> LENGTH: 9
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 33

Gly Asp Ile Ser Val Val Tyr Gly Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 34

Asp Ile Ser Val Val Tyr Gly Leu Arg
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 35

Ile Ser Val Val Tyr Gly Leu Arg Ser
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 36

Val Asp Thr Tyr Asp Gly Asp Ile
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 37

Asp Thr Tyr Asp Gly Asp Ile Ser
1               5
```

```
<210> SEQ ID NO 38
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 38

Thr Tyr Asp Gly Asp Ile Ser Val
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 39

Tyr Asp Gly Asp Ile Ser Val Val
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 40

Asp Gly Asp Ile Ser Val Val Tyr
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 41

Gly Asp Ile Ser Val Val Tyr Gly
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide
```

```
<400> SEQUENCE: 42

Asp Ile Ser Val Val Tyr Gly Leu
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 43

Ile Ser Val Val Tyr Gly Leu Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 44

Val Asp Thr Tyr Asp Gly Asp
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 45

Asp Thr Tyr Asp Gly Asp Ile
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 46

Thr Tyr Asp Gly Asp Ile Ser
1               5

<210> SEQ ID NO 47
<211> LENGTH: 7
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 47

Tyr Asp Gly Asp Ile Ser Val
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 48

Asp Gly Asp Ile Ser Val Val
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 49

Gly Asp Ile Ser Val Val Tyr
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 50

Asp Ile Ser Val Val Tyr Gly
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 51

Ile Ser Val Val Tyr Gly Leu
1               5
```

```
<210> SEQ ID NO 52
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 52

Asp Thr Tyr Asp Gly Asp
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 53

Thr Tyr Asp Gly Asp Ile
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 54

Tyr Asp Gly Asp Ile Ser
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 55

Asp Gly Asp Ile Ser Val
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide
```

```
<400> SEQUENCE: 56

Gly Asp Ile Ser Val Val
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 57

Asp Ile Ser Val Val Tyr
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 58

Ile Ser Val Val Tyr Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 59

Thr Tyr Asp Gly Asp
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 60

Tyr Asp Gly Asp Ile
1               5

<210> SEQ ID NO 61
<211> LENGTH: 5
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 61

Asp Gly Asp Ile Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 62

Gly Asp Ile Ser Val
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 63

Asp Ile Ser Val Val
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 64

Ile Ser Val Val Tyr
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 65

Ser Val Val Tyr Gly
1               5
```

```
<210> SEQ ID NO 66
<211> LENGTH: 300
<212> TYPE: PRT
<213> ORGANISM: Homo sapiens
<220> FEATURE:
<221> NAME/KEY: MISC_FEATURE
<222> LOCATION: (1)..(300)
<223> OTHER INFORMATION: Wildtype human osteopontin

<400> SEQUENCE: 66

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
        115                 120                 125

Thr Glu Val Phe Thr Pro Val Val Pro Thr Val Asp Thr Tyr Asp Gly
    130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Glu Asp Lys His Leu Lys Phe Arg Ile
        275                 280                 285

Ser His Glu Leu Asp Ser Ala Ser Ser Glu Val Asn
    290                 295                 300

<210> SEQ ID NO 67
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide, FOL-002
```

```
<400> SEQUENCE: 67

Val Asp Thr Tyr Asp Gly Arg Gly Asp Ser Val Val Tyr Gly Leu Arg
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide
<220> FEATURE:
<221> NAME/KEY: MISC_FEATURE
<222> LOCATION: (3)..(3)
<223> OTHER INFORMATION: Z is T or V
<220> FEATURE:
<221> NAME/KEY: MISC_FEATURE
<222> LOCATION: (4)..(4)
<223> OTHER INFORMATION: Z is Y or P
<220> FEATURE:
<221> NAME/KEY: MISC_FEATURE
<222> LOCATION: (5)..(5)
<223> OTHER INFORMATION: Z is D or N
<220> FEATURE:
<221> NAME/KEY: MISC_FEATURE
<222> LOCATION: (7)..(7)
<223> OTHER INFORMATION: Z is D or G
<220> FEATURE:
<221> NAME/KEY: MISC_FEATURE
<222> LOCATION: (8)..(8)
<223> OTHER INFORMATION: Z is I or G
<220> FEATURE:
<221> NAME/KEY: MISC_FEATURE
<222> LOCATION: (10)..(10)
<223> OTHER INFORMATION: Z is V or L
<220> FEATURE:
<221> NAME/KEY: MISC_FEATURE
<222> LOCATION: (11)..(11)
<223> OTHER INFORMATION: Z is V or A

<400> SEQUENCE: 68

Val Asp Glx Glx Glx Gly Glx Glx Ser Glx Glx Tyr Gly Leu Arg
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide, FOL-004

<400> SEQUENCE: 69

Val Asp Val Pro Asn Gly Asp Ile Ser Leu Ala Tyr Gly Leu Arg
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide
```

```
<400> SEQUENCE: 70

Asp Val Pro Asn Gly Asp Ile Ser Leu Ala Tyr Gly Leu Arg Ser
1               5                   10                  15

<210> SEQ ID NO 71
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(14)
<223> OTHER INFORMATION: peptide

<400> SEQUENCE: 71

Val Asp Val Pro Asn Gly Asp Ile Ser Leu Ala Tyr Gly Leu
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(14)
<223> OTHER INFORMATION: peptide

<400> SEQUENCE: 72

Asp Val Pro Asn Gly Asp Ile Ser Leu Ala Tyr Gly Leu Arg
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(14)
<223> OTHER INFORMATION: peptide

<400> SEQUENCE: 73

Val Pro Asn Gly Asp Ile Ser Leu Ala Tyr Gly Leu Arg Ser
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide, FOL-017

<400> SEQUENCE: 74

Val Asp Val Pro Asn Gly Asp Ile Ser Leu Ala Tyr Gly
1               5                   10

<210> SEQ ID NO 75
<211> LENGTH: 13
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 75

Asp Val Pro Asn Gly Asp Ile Ser Leu Ala Tyr Gly Leu
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 76

Val Pro Asn Gly Asp Ile Ser Leu Ala Tyr Gly Leu Arg
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 77

Pro Asn Gly Asp Ile Ser Leu Ala Tyr Gly Leu Arg Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 78

Val Asp Val Pro Asn Gly Asp Ile Ser Leu Ala Tyr
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 79

Asp Val Pro Asn Gly Asp Ile Ser Leu Ala Tyr Gly
1               5                   10
```

```
<210> SEQ ID NO 80
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 80

Val Pro Asn Gly Asp Ile Ser Leu Ala Tyr Gly Leu
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 81

Pro Asn Gly Asp Ile Ser Leu Ala Tyr Gly Leu Arg
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: peptide

<400> SEQUENCE: 82

Asn Gly Asp Ile Ser Leu Ala Tyr Gly Leu Arg Ser
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 83

Val Asp Val Pro Asn Gly Asp Ile Ser Leu Ala
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide
```

```
<400> SEQUENCE: 84

Asp Val Pro Asn Gly Asp Ile Ser Leu Ala Tyr
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 85

Val Pro Asn Gly Asp Ile Ser Leu Ala Tyr Gly
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 86

Pro Asn Gly Asp Ile Ser Leu Ala Tyr Gly Leu
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 87

Asn Gly Asp Ile Ser Leu Ala Tyr Gly Leu Arg
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(11)
<223> OTHER INFORMATION: peptide

<400> SEQUENCE: 88

Gly Asp Ile Ser Leu Ala Tyr Gly Leu Arg Ser
1               5                   10

<210> SEQ ID NO 89
<211> LENGTH: 10
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 89

Val Asp Val Pro Asn Gly Asp Ile Ser Leu
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 90

Asp Val Pro Asn Gly Asp Ile Ser Leu Ala
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 91

Val Pro Asn Gly Asp Ile Ser Leu Ala Tyr
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 92

Pro Asn Gly Asp Ile Ser Leu Ala Tyr Gly
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 93

Asn Gly Asp Ile Ser Leu Ala Tyr Gly Leu
1               5                   10
```

```
<210> SEQ ID NO 94
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide, FOL-009

<400> SEQUENCE: 94

Gly Asp Ile Ser Leu Ala Tyr Gly Leu Arg
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(10)
<223> OTHER INFORMATION: peptide

<400> SEQUENCE: 95

Asp Ile Ser Leu Ala Tyr Gly Leu Arg Ser
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide
<220> FEATURE:
<221> NAME/KEY: MISC_FEATURE
<222> LOCATION: (1)..(9)
<223> OTHER INFORMATION: peptide, FOL-019

<400> SEQUENCE: 96

Val Asp Val Pro Asn Gly Asp Ile Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 97

Asp Val Pro Asn Gly Asp Ile Ser Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic sequence
```

```
<220> FEATURE:
<221> NAME/KEY: MISC_FEATURE
<222> LOCATION: (1)..(9)
<223> OTHER INFORMATION: peptide

<400> SEQUENCE: 98

Val Pro Asn Gly Asp Ile Ser Leu Ala
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 99

Pro Asn Gly Asp Ile Ser Leu Ala Tyr
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 100

Asn Gly Asp Ile Ser Leu Ala Tyr Gly
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 101

Gly Asp Ile Ser Leu Ala Tyr Gly Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 102

Asp Ile Ser Leu Ala Tyr Gly Leu Arg
1               5
```

```
<210> SEQ ID NO 103
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(9)
<223> OTHER INFORMATION: peptide

<400> SEQUENCE: 103

Ile Ser Leu Ala Tyr Gly Leu Arg Ser
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 104

Val Asp Val Pro Asn Gly Asp Ile
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 105

Asp Val Pro Asn Gly Asp Ile Ser
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 106

Val Pro Asn Gly Asp Ile Ser Leu
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide
```

```
<400> SEQUENCE: 107

Pro Asn Gly Asp Ile Ser Leu Ala
1               5

<210> SEQ ID NO 108
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 108

Asn Gly Asp Ile Ser Leu Ala Tyr
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 109

Gly Asp Ile Ser Leu Ala Tyr Gly
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 110

Asp Ile Ser Leu Ala Tyr Gly Leu
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 111

Ile Ser Leu Ala Tyr Gly Leu Arg
1               5

<210> SEQ ID NO 112
<211> LENGTH: 7
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 112

Val Asp Val Pro Asn Gly Asp
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 113

Asp Val Pro Asn Gly Asp Ile
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 114

Val Pro Asn Gly Asp Ile Ser
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 115

Pro Asn Gly Asp Ile Ser Leu
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 116

Asn Gly Asp Ile Ser Leu Ala
1               5
```

```
<210> SEQ ID NO 117
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 117

Gly Asp Ile Ser Leu Ala Tyr
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 118

Asp Ile Ser Leu Ala Tyr Gly
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(7)
<223> OTHER INFORMATION: peptide

<400> SEQUENCE: 119

Ile Ser Leu Ala Tyr Gly Leu
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 120

Asp Val Pro Asn Gly Asp
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide
```

```
<400> SEQUENCE: 121

Val Pro Asn Gly Asp Ile
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 122

Pro Asn Gly Asp Ile Ser
1               5

<210> SEQ ID NO 123
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 123

Asn Gly Asp Ile Ser Leu
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 124

Gly Asp Ile Ser Leu Ala
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 125

Asp Ile Ser Leu Ala Tyr
1               5

<210> SEQ ID NO 126
<211> LENGTH: 6
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: MISC_FEATURE
<222> LOCATION: (1)..(6)
<223> OTHER INFORMATION: peptide

<400> SEQUENCE: 126

Ile Ser Leu Ala Tyr Gly
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 127

Val Pro Asn Gly Asp
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 128

Pro Asn Gly Asp Ile
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 129

Asn Gly Asp Ile Ser
1               5

<210> SEQ ID NO 130
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 130

Gly Asp Ile Ser Leu
1               5
```

```
<210> SEQ ID NO 131
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 131

Asp Ile Ser Leu Ala
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 132

Ile Ser Leu Ala Tyr
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: peptide

<400> SEQUENCE: 133

Ser Leu Ala Tyr Gly
1               5

<210> SEQ ID NO 134
<211> LENGTH: 294
<212> TYPE: PRT
<213> ORGANISM: Mus musculus
<220> FEATURE:
<221> NAME/KEY: MISC_FEATURE
<222> LOCATION: (1)..(294)
<223> OTHER INFORMATION: Wildtype murine osteopontin

<400> SEQUENCE: 134

Met Arg Leu Ala Val Ile Cys Phe Cys Leu Phe Gly Ile Ala Ser Ser
1               5                   10                  15

Leu Pro Val Lys Val Thr Asp Ser Gly Ser Ser Glu Glu Lys Leu Tyr
            20                  25                  30

Ser Leu His Pro Asp Pro Ile Ala Thr Trp Leu Val Pro Asp Pro Ser
        35                  40                  45

Gln Lys Gln Asn Leu Leu Ala Pro Gln Asn Ala Val Ser Ser Glu Glu
    50                  55                  60

Lys Asp Asp Phe Lys Gln Glu Thr Leu Pro Ser Asn Ser Asn Glu Ser
65                  70                  75                  80

His Asp His Met Asp Asp Asp Asp Asp Asp Asp Asp Asp Gly Asp
                85                  90                  95
```

```
His Ala Glu Ser Glu Asp Ser Val Asp Ser Asp Ser Asp Glu Ser
                100                 105                 110

His His Ser Asp Glu Ser Asp Glu Thr Val Thr Ala Ser Thr Gln Ala
            115                 120                 125

Asp Thr Phe Thr Pro Ile Val Pro Thr Val Asp Val Pro Asn Gly Arg
130                 135                 140

Gly Asp Ser Leu Ala Tyr Gly Leu Arg Ser Lys Ser Arg Ser Phe Gln
145                 150                 155                 160

Val Ser Asp Glu Gln Tyr Pro Asp Ala Thr Asp Glu Asp Leu Thr Ser
                165                 170                 175

His Met Lys Ser Gly Glu Ser Lys Glu Ser Leu Asp Val Ile Pro Val
            180                 185                 190

Ala Gln Leu Leu Ser Met Pro Ser Asp Gln Asp Asn Asn Gly Lys Gly
        195                 200                 205

Ser His Glu Ser Ser Gln Leu Asp Glu Pro Ser Leu Glu Thr His Arg
    210                 215                 220

Leu Glu His Ser Lys Glu Ser Gln Glu Ser Ala Asp Gln Ser Asp Val
225                 230                 235                 240

Ile Asp Ser Gln Ala Ser Ser Lys Ala Ser Leu Glu His Gln Ser His
                245                 250                 255

Lys Phe His Ser His Lys Asp Lys Leu Val Leu Asp Pro Lys Ser Lys
            260                 265                 270

Glu Asp Asp Arg Tyr Leu Lys Phe Arg Ile Ser His Glu Leu Glu Ser
        275                 280                 285

Ser Ser Ser Glu Val Asn
    290

<210> SEQ ID NO 135
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide, FOL-001

<400> SEQUENCE: 135

Val Asp Val Pro Asn Gly Arg Gly Asp Ser Leu Ala Tyr Gly Leu Arg
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide, FOL-014

<400> SEQUENCE: 136

Lys Pro Leu Ala Glu Ile Asp Ser Ile Glu Leu Ser Tyr Gly Ile Lys
1               5                   10                  15

<210> SEQ ID NO 137
<211> LENGTH: 16
<212> TYPE: PRT
<213> ORGANISM: Artificial Sequence
```

<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide, FOL-003

<400> SEQUENCE: 137

Gly Asp Pro Asn Asp Gly Arg Gly Asp Ser Val Val Tyr Gly Leu Arg
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide, FOL-026

<400> SEQUENCE: 138

Val Asp Thr Tyr Asp Gly Gly Ile Ser Val Val Tyr Gly Leu Arg
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide, FOL-027

<400> SEQUENCE: 139

Val Asp Thr Tyr Asp Gly Asp Gly Ser Val Val Tyr Gly Leu Arg
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide
<220> FEATURE:
<221> NAME/KEY: MISC_FEATURE
<222> LOCATION: (2)..(2)
<223> OTHER INFORMATION: X is C, P or G
<220> FEATURE:
<221> NAME/KEY: MISC_FEATURE
<222> LOCATION: (5)..(5)
<223> OTHER INFORMATION: X is E or G
<220> FEATURE:
<221> NAME/KEY: MISC_FEATURE
<222> LOCATION: (6)..(6)
<223> OTHER INFORMATION: X is C, D or I
<220> FEATURE:
<221> NAME/KEY: MISC_FEATURE
<222> LOCATION: (7)..(7)
<223> OTHER INFORMATION: X is D, I, S or G
<220> FEATURE:
<221> NAME/KEY: MISC_FEATURE
<222> LOCATION: (8)..(8)
<223> OTHER INFORMATION: X is S, D or G

```
<220> FEATURE:
<221> NAME/KEY: MISC_FEATURE
<222> LOCATION: (10)..(10)
<223> OTHER INFORMATION: X is E or G
<220> FEATURE:
<221> NAME/KEY: MISC_FEATURE
<222> LOCATION: (12)..(12)
<223> OTHER INFORMATION: X is S or T

<400> SEQUENCE: 140

Lys Xaa Leu Ala Xaa Xaa Xaa Ile Xaa Leu Xaa Tyr Gly Ile Lys
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 141

Lys Cys Leu Ala Glu Cys Asp Ser Ile Glu Leu Ser Tyr Gly Ile Lys
1               5                   10                  15

<210> SEQ ID NO 142
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(8)
<223> OTHER INFORMATION: peptide

<400> SEQUENCE: 142

Cys Leu Ala Glu Ile Asp Ser Cys
1               5

<210> SEQ ID NO 143
<211> LENGTH: 18
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(18)
<223> OTHER INFORMATION: peptide

<400> SEQUENCE: 143

Cys Phe Lys Pro Leu Ala Glu Ile Asp Ser Ile Glu Cys Ser Tyr Gly
1               5                   10                  15

Ile Lys

<210> SEQ ID NO 144
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide
```

```
<400> SEQUENCE: 144

Lys Pro Leu Ala Glu Asp Ile Ser Ile Glu Leu Ser Tyr Gly Ile Lys
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 145

Lys Pro Leu Ala Glu Ile Ser Asp Ile Glu Leu Ser Tyr Gly Ile Lys
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 146

Lys Pro Leu Ala Glu Ile Gly Asp Ile Glu Leu Ser Tyr Gly Ile Lys
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide

<400> SEQUENCE: 147

Lys Pro Leu Ala Glu Gly Asp Ile Glu Leu Ser Tyr Gly Ile Lys
1               5                   10                  15

<210> SEQ ID NO 148
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 148

Lys Pro Leu Ala Glu Ile Glu Leu Ser Tyr Gly Ile Lys
1               5                   10

<210> SEQ ID NO 149
<211> LENGTH: 16
<212> TYPE: PRT
<213> ORGANISM: Artificial Sequence
```

-continued

```
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 149

Lys Pro Leu Ala Glu Ile Asp Ser Ile Glu Leu Thr Tyr Gly Ile Lys
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 150

Lys Pro Leu Ala Glu Ile Asp Gly Ile Glu Leu Ser Tyr Gly Ile Lys
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 151

Lys Pro Leu Ala Glu Ile Asp Gly Ile Glu Leu Thr Tyr Gly Ile Lys
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 152

Lys Pro Leu Ala Glu Ile Gly Ser Ile Glu Leu Ser Tyr Gly Ile Lys
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 153

Lys Gly Leu Ala Glu Ile Asp Ser Ile Glu Leu Ser Tyr Gly Ile Lys
1               5                   10                  15
```

```
<210> SEQ ID NO 154
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 154

Lys Pro Leu Ala Gly Ile Asp Ser Ile Gly Leu Ser Tyr Gly Ile Lys
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(16)
<223> OTHER INFORMATION: peptide

<400> SEQUENCE: 155

Lys Cys Leu Ala Glu Ile Asp Ser Cys Glu Leu Ser Tyr Gly Ile Lys
1               5                   10                  15

<210> SEQ ID NO 156
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: peptide

<400> SEQUENCE: 156

Cys Phe Lys Pro Leu Ala Glu Ile Asp Ser Ile Glu Cys
1               5                   10

<210> SEQ ID NO 157
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide

<400> SEQUENCE: 157

Val Asp Val Pro Glu Gly Asp Ile Ser Leu Ala Tyr Gly Leu Arg
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide
```

<400> SEQUENCE: 158

Leu Asp Gly Leu Val Arg Ala Tyr Asp Asn Ile Ser Pro Val Gly
1               5                   10                  15

<210> SEQ ID NO 159
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(14)
<223> OTHER INFORMATION: peptide

<400> SEQUENCE: 159

Gly Asp Pro Asn Gly Asp Ile Ser Val Val Tyr Gly Leu Arg
1               5                   10

<210> SEQ ID NO 160
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide

<400> SEQUENCE: 160

Val Asp Val Pro Asn Gly Asp Ile Ser Leu Ala Tyr Arg Leu Arg
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(15)
<223> OTHER INFORMATION: peptide

<400> SEQUENCE: 161

Val Asp Val Pro Glu Gly Asp Ile Ser Leu Ala Tyr Arg Leu Arg
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide
<220> FEATURE:
<221> NAME/KEY: MISC_FEATURE
<222> LOCATION: (2)..(2)
<223> OTHER INFORMATION: X is C, P or G
<220> FEATURE:
<221> NAME/KEY: MISC_FEATURE
<222> LOCATION: (5)..(5)
<223> OTHER INFORMATION: X is E or G
<220> FEATURE:
<221> NAME/KEY: MISC_FEATURE
<222> LOCATION: (6)..(6)
<223> OTHER INFORMATION: X is C, I or absent

```
<220> FEATURE:
<221> NAME/KEY: MISC_FEATURE
<222> LOCATION: (7)..(7)
<223> OTHER INFORMATION: X is D, G or absent
<220> FEATURE:
<221> NAME/KEY: MISC_FEATURE
<222> LOCATION: (8)..(8)
<223> OTHER INFORMATION: X is S, G or absent
<220> FEATURE:
<221> NAME/KEY: MISC_FEATURE
<222> LOCATION: (10)..(10)
<223> OTHER INFORMATION: X is E or G

<400> SEQUENCE: 162

Lys Xaa Leu Ala Xaa Xaa Xaa Xaa Ile Xaa Leu Ser Tyr Gly Ile Lys
1               5                   10                  15

<210> SEQ ID NO 163
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide
<220> FEATURE:
<221> NAME/KEY: MISC_FEATURE
<222> LOCATION: (2)..(2)
<223> OTHER INFORMATION: X is C, P or G
<220> FEATURE:
<221> NAME/KEY: MISC_FEATURE
<222> LOCATION: (5)..(5)
<223> OTHER INFORMATION: X is E or G
<220> FEATURE:
<221> NAME/KEY: MISC_FEATURE
<222> LOCATION: (10)..(10)
<223> OTHER INFORMATION: X is E or G

<400> SEQUENCE: 163

Lys Xaa Leu Ala Xaa Ile Xaa Leu Ser Tyr Gly Ile Lys
1               5                   10

<210> SEQ ID NO 164
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide
<220> FEATURE:
<221> NAME/KEY: MISC_FEATURE
<222> LOCATION: (1)..(5)
<223> OTHER INFORMATION: Z is E or N
<220> FEATURE:
<221> NAME/KEY: MISC_FEATURE
<222> LOCATION: (5)..(5)
<223> OTHER INFORMATION: Z is E or N
<220> FEATURE:
<221> NAME/KEY: MISC_FEATURE
<222> LOCATION: (13)..(13)
<223> OTHER INFORMATION: Z is R or G

<400> SEQUENCE: 164

Val Asp Val Pro Glx Gly Asp Ile Ser Leu Ala Tyr Glx Leu Arg
1               5                   10                  15
```

```
<210> SEQ ID NO 165
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide
<220> FEATURE:
<221> NAME/KEY: MISC_FEATURE
<222> LOCATION: (7)..(7)
<223> OTHER INFORMATION: Z is D or G
<220> FEATURE:
<221> NAME/KEY: MISC_FEATURE
<222> LOCATION: (8)..(8)
<223> OTHER INFORMATION: Z is I or G

<400> SEQUENCE: 165

Val Asp Thr Tyr Asp Gly Glx Glx Ser Val Val Tyr Gly Leu Arg
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide
<220> FEATURE:
<221> NAME/KEY: MISC_FEATURE
<222> LOCATION: (5)..(5)
<223> OTHER INFORMATION: Z is D or G
<220> FEATURE:
<221> NAME/KEY: MISC_FEATURE
<222> LOCATION: (6)..(6)
<223> OTHER INFORMATION: Z is D or G
<220> FEATURE:
<221> NAME/KEY: MISC_FEATURE
<222> LOCATION: (7)..(7)
<223> OTHER INFORMATION: Z is I or R
<220> FEATURE:
<221> NAME/KEY: MISC_FEATURE
<222> LOCATION: (8)..(8)
<223> OTHER INFORMATION: Z is G or absent
<220> FEATURE:
<221> NAME/KEY: MISC_FEATURE
<222> LOCATION: (9)..(9)
<223> OTHER INFORMATION: Z is D or absent

<400> SEQUENCE: 166

Gly Asp Pro Asn Glx Glx Glx Glx Ser Val Val Tyr Gly Leu Arg
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide
<220> FEATURE:
<221> NAME/KEY: MISC_FEATURE
<222> LOCATION: (2)..(2)
<223> OTHER INFORMATION: Z is beta D
```

```
<400> SEQUENCE: 167

Val Glx Thr Tyr Asp Gly Asp Ile Ser Val Val Tyr Gly Leu Arg
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide
<220> FEATURE:
<221> NAME/KEY: MISC_FEATURE
<222> LOCATION: (5)..(5)
<223> OTHER INFORMATION: Z is beta D

<400> SEQUENCE: 168

Val Asp Thr Tyr Glx Gly Asp Ile Ser Val Val Tyr Gly Leu Arg
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide
<220> FEATURE:
<221> NAME/KEY: MISC_FEATURE
<222> LOCATION: (7)..(7)
<223> OTHER INFORMATION: Z is beta D

<400> SEQUENCE: 169

Val Asp Thr Tyr Asp Gly Glx Ile Ser Val Val Tyr Gly Leu Arg
1               5                   10                  15
```

PEPTIDES FOR TREATMENT OF DIABETES

CROSS REFERENCE TO RELATED APPLICATIONS

This application is a continuation of International Patent Application No: PCT/EP2018/061547 filed May 4, 2018 and designating the United States of America, and which claims priority to European Patent Application No: 17169500.0 filed May 4, 2017, the entire contents of each of which are incorporated herein by reference.

TECHNICAL FIELD

The present disclosure relates to peptides useful for treatment of diabetes and associated disorders.

BACKGROUND

The peptide hormone insulin, which is produced by β-cells in the islets of Langerhans in the pancreas, is released in response to increasing blood glucose levels. Thus, glucose is removed from the blood by insulin dependent stimulation of glucose transporters located in the cell membranes of the target tissue, e.g. adipose tissue, skeletal muscle and liver. Insulin exerts its biological effects by binding to and activating the membrane-bound insulin receptor (IR), thereby initiating a cascade of intracellular signalling events, which regulate multiple biological processes such as glucose and lipid metabolism.

Currently, the treatment of diabetes, both type 1 and type 2 diabetes, relies primarily on insulin treatment. A complement to insulin treatment is long-acting glucagon-like peptide-1 (GLP-1) receptor agonists, i.e. derivatives that act on the same receptor as GLP-1. GLP-1 is a metabolic hormone that stimulates insulin secretion. Besides increasing insulin secretion from the pancreas in a glucose-dependent manner, GLP-1 is known to increase insulin-sensitivity in both α- and β-cells; to increase β-cell mass and insulin expression, post-translational modification, and secretion; and to decrease glucagon secretion from the pancreas. Other medications used complementary to insulin treatment for the purpose of lowering plasma glucose levels include DPP-IV inhibitors, Metformin, SGLT-2 inhibitors and sulfonylurea.

Certain drawbacks are associated with long term use of insulin, such as weight gain and increased risks of cancer and hypoglycaemia. Thus, there is a growing demand in the field for novel non-insulin compounds capable of, not only treating diabetes, by addressing insulin resistance and hyperglycemia, but also reducing associated and consequential complications.

Identification of novel compounds that can restore glucose metabolism and treat diabetes and related disorders is thus highly relevant. Multiple approaches can be contemplated, albeit none of which are obvious to the person of skill in the art.

SUMMARY

The present inventors have found peptides which stimulate β-cell proliferation, have the ability to rescue β-cell from apoptosis induced by glucotoxic conditions, and stimulate insulin secretion from rat INS-1 β-cells as well as isolated mouse pancreatic islets. Furthermore, the present inventors found that in a glucose tolerance test, the peptides lowered plasma glucose levels in vivo and delayed onset of diabetes disease in BB lyp/lyp rats, a model for type 1 diabetes. Hence, the peptides of the present disclosure are suitable for use in the treatment of endocrine, nutritional and metabolic diseases and disorders.

In one aspect, the present disclosure relates to an agent comprising or consisting of:

a) a peptide or peptide analog, wherein the peptide or peptide analog comprises an amino acid sequence of the general formula:

$$KX_2LAX_5X_6X_7X_8IX_{10}LX_{12}YGIK \quad \text{(SEQ ID NO: 140)}$$

wherein:
 $X_2$ is C, P or G;
 $X_5$ is E or G;
 $X_6$ is C, D or I;
 $X_7$ is D, I, S or G;
 $X_8$ is S, D or G;
 $X_{10}$ is E or G;
 $X_{12}$ is S or T;
 with the proviso that if $X_{12}$ is T then the peptide comprises no more than 25 amino acids; and
 with the proviso that if $X_2$ is P, $X_5$ is E, $X_6$ is I, $X_7$ is D, $X_8$ is S, $X_{10}$ is E and $X_{12}$ is S, the peptide comprises no more than 85 amino acid residues.
 or a biologically active fragment and/or variant thereof, wherein said biologically active fragment and/or variant is selected from the group consisting of CLAEIDSC (SEQ ID NO: 142), CFKPLAEIDSIECSYGIK (SEQ ID NO: 143), KPLAEGDIELSYGIK (SEQ ID NO: 147), KPLAEIELSYGIK (SEQ ID NO: 148), KCLAEIDSCELSYGIK (SEQ ID NO: 155), and CFKPLAEIDSIEC (SEQ ID NO: 156);

b) a polynucleotide encoding upon expression, the peptide of a);

c) a vector comprising the polynucleotide of b); and d) a cell comprising the polynucleotide of b), or the vector of c).

In one aspect, the present disclosure relates to an agent comprising:

a) a peptide or peptide analog comprising or consisting of the amino acid sequence GDPNDGRGDSVVYGLR (SEQ ID NO: 137), VDTYDGGISVVYGLR (SEQ ID NO: 138), and VDTYDGDGSVVYGLR (SEQ ID NO: 139). VDVPEGDISLAYGLR (SEQ ID NO: 157), LDGLVRAYDNISPVG (SEQ ID NO: 158), GDPNGDISVVYGLR (SEQ ID NO: 159), VDVPNGDISLAYRLR (SEQ ID NO: 160) VDVPEGDISLAYRLR (SEQ ID NO: 161), V(beta-D)TYDGDISVVYGLR (SEQ ID NO:167), VDTY(beta-D)GDISVVYGLR (SEQ ID NO: 168), VDTYDG(beta-D)ISVVYGLR (SEQ ID NO:169);

b) a polynucleotide encoding upon expression, the peptide of a);

c) a vector comprising the polynucleotide of b); and d) a cell comprising the polynucleotide of b), or the vector of c).

In one aspect, the present disclosure relates to a composition comprising the agent described herein above.

In one aspect, the present disclosure relates to an agent or a composition comprising said agent, for use as a medicament.

In one aspect, the present disclosure relates to an agent comprising:
a) (i) a peptide or a peptide analog, wherein the peptide or the peptide analog comprises or consists of an amino acid sequence of the general formula:

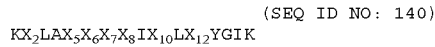
(SEQ ID NO: 140)

wherein:
$X_2$ is C, P or G;
$X_5$ is E or G;
$X_6$ is C, D or I;
$X_7$ is D, I, S or G;
$X_8$ is S, D or G;
$X_{10}$ is E or G;
$X_{12}$ is S or T;
with the proviso that if $X_{12}$ is T, the peptide comprises no more than 25 amino acid residues;
(ii) a peptide, wherein the peptide comprises an amino acid sequence of the general formula:

(SEQ ID NO: 68)

wherein:
$Z_3$ is T or V;
$Z_4$ is Y or P;
$Z_5$ is D or N;
$Z_7$ is D or G;
$Z_8$ is I or G;
$Z_{10}$ is V or L;
$Z_{11}$ is V or A;
(iii) a peptide, wherein the peptide comprises or consists of an amino acid sequence selected from the group consisting of KCLAECDSIELSYGIK (SEQ ID NO: 141), CLAEIDSC (SEQ ID NO: 142), CFKPLAEIDSIECSYGIK (SEQ ID NO: 143), KPLAEIELSYGIK (SEQ ID NO: 148), KCLAEIDSCELSYGIK (SEQ ID NO: 155) and CFKPLAEIDSIEC (SEQ ID NO: 156);
b) a polynucleotide encoding upon expression, the peptide of a);
c) a vector comprising the polynucleotide of b); and
d) a cell comprising the polynucleotide of b), or the vector of c).
for use in the treatment of an endocrine disease, a nutritional disease and/or a metabolic disease in a mammal.

In one aspect, the present disclosure concerns a method for treating an endocrine disease a nutritional disease and/or a metabolic disease, the method comprising administering a therapeutically effective amount of an agent described herein, to an individual in need thereof.

In one aspect, the present disclosure concerns the use of an agent as described herein for the manufacture of a medicament for the treatment of an endocrine disease a nutritional disease and/or a metabolic disease.

In one aspect, the present disclosure concerns a method for delaying onset of diabetes, the method comprising administering a therapeutically effective amount of an agent described herein, to an individual in need thereof.

In one aspect, the present disclosure concerns a method for decreasing blood glucose levels, the method comprising administering a therapeutically effective amount of an agent described herein, to an individual in need thereof.

In one aspect, the present disclosure concerns a method, e.g. an in vitro method, for improving beta cell morphology, the method comprising administering a therapeutically effective amount of an agent described herein, to an individual in need thereof.

In one aspect, the present disclosure concerns a method for improving beta cell viability, the method comprising administering a therapeutically effective amount of an agent described herein, to an individual in need thereof.

In one aspect, the present disclosure concerns the use of agent described herein for the preparation of a diagnostic composition for the diagnosis of a disease, disorder or damage of the pancreas in an individual.

Figure 1:
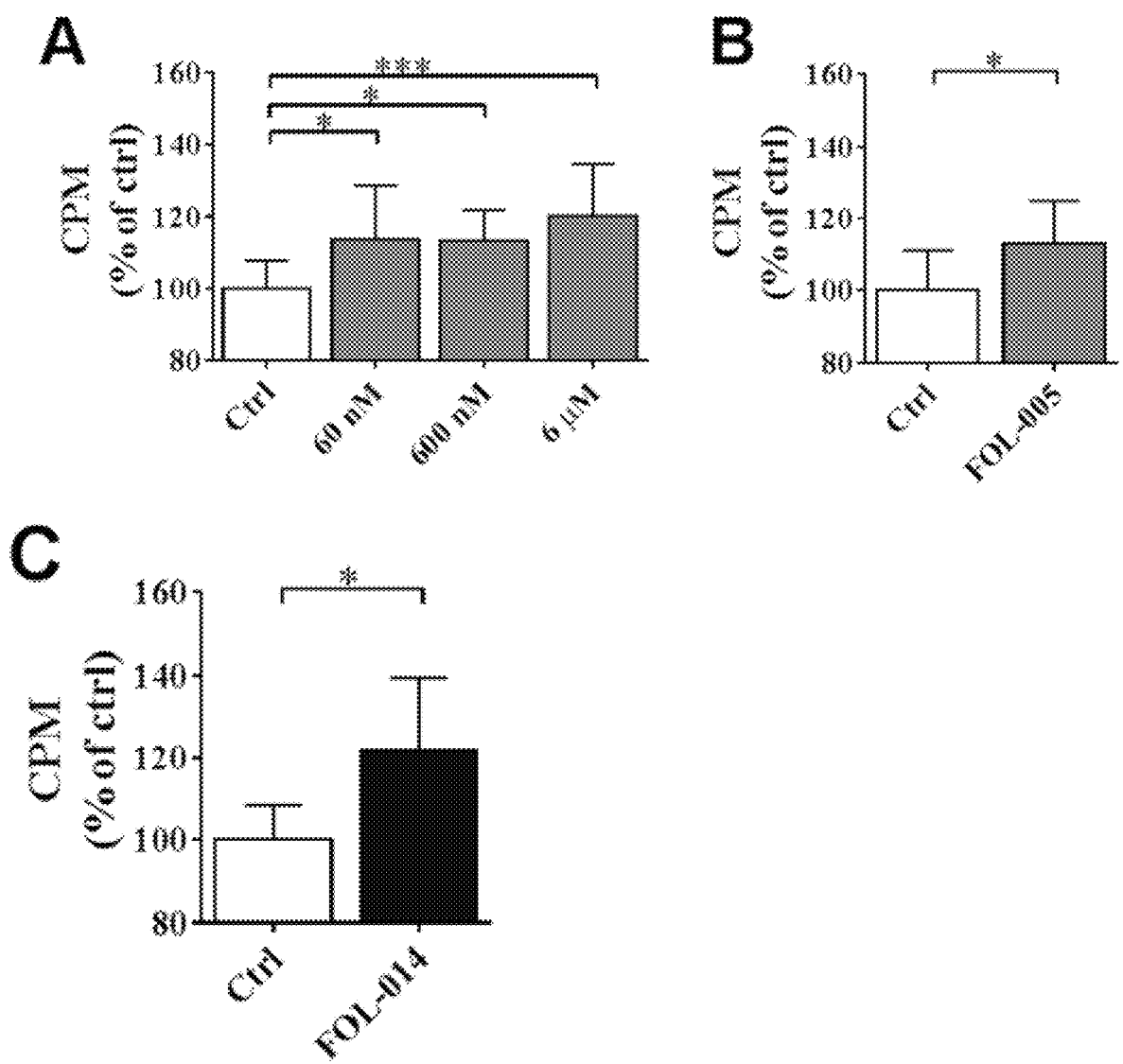
FIG. 1. FOL-005 and FOL-014 induced proliferation of β-cells
Figure 10:
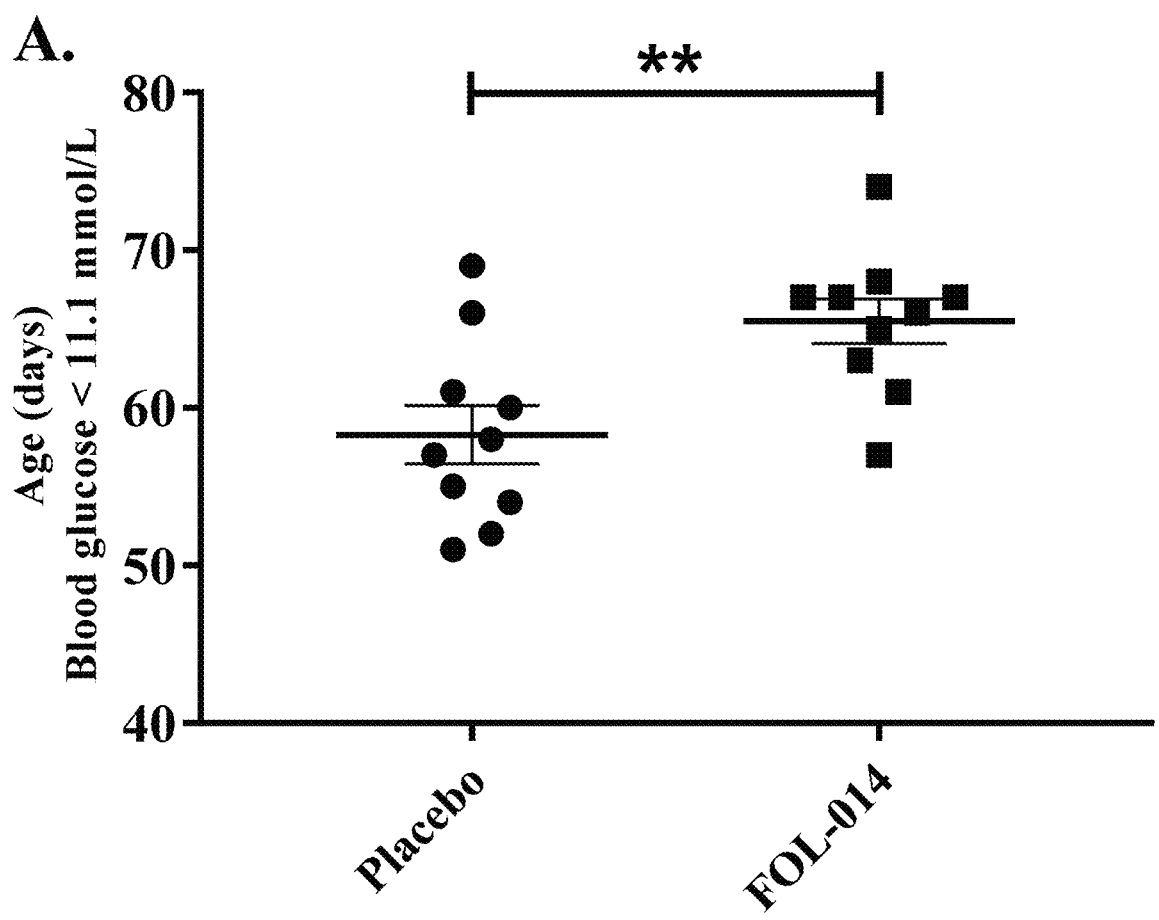

Addition of increasing concentrations of FOL-005 in solution induced increasing proliferation of INS-1 cells after 48 hours (FIG. 1A). Wells coated with FOL-005 and blocked with Bovine Serum Albumin (BSA) induced more proliferation of β-cells compared to only BSA coated control (ctrl) wells (FIG. 1B). Wells pre-coated with FOL-014 and blocked with BSA induced more proliferation compared to only BSA coated wells (FIG. 10). Data is presented as counts per minute (CPM) relative unstimulated control (ctrl) cells. Mean±SD are presented for 10-12 different observations in each group.

Figure 2:
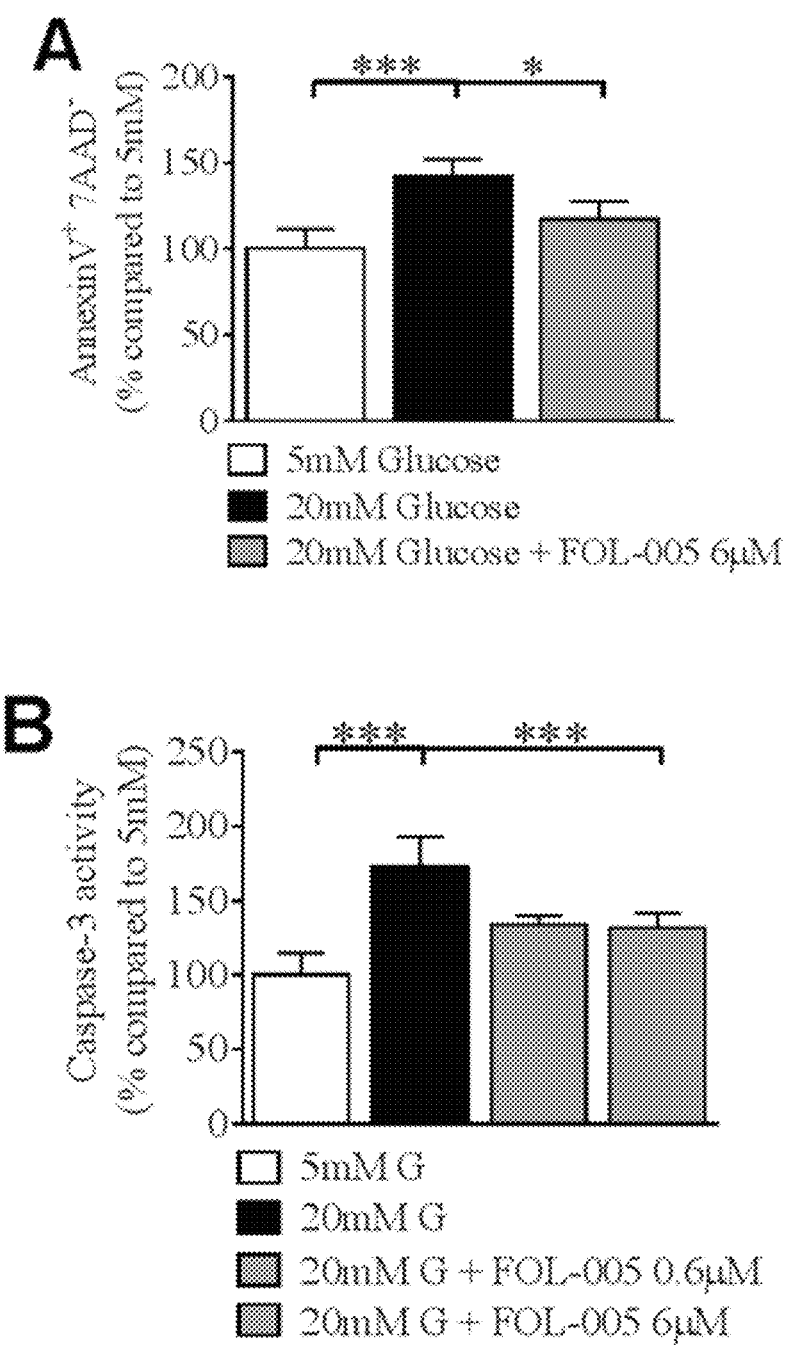

FIG. 2. FOL-005 protected β-cells against glucotoxicity

INS-1 cells incubated during 48 h in 20 mM glucose displayed more apoptotic cells (Annexin V positive) compared to cells incubated at 5 mM glucose. Addition of FOL-005 to cells incubated with 20 mM glucose reduced the level of apoptotic cells compared to 20 mM glucose alone (FIG. 2A). Apoptosis measured by caspase-3 activity was increased in INS-1 cells at 20 mM compared to 5 mM glucose. Addition of FOL-005 diminished the rate of glucotoxicity-induced caspase-3 activity (FIG. 2B). Mean±SD are presented for 4-8 different observations in each group.

Figure 3:
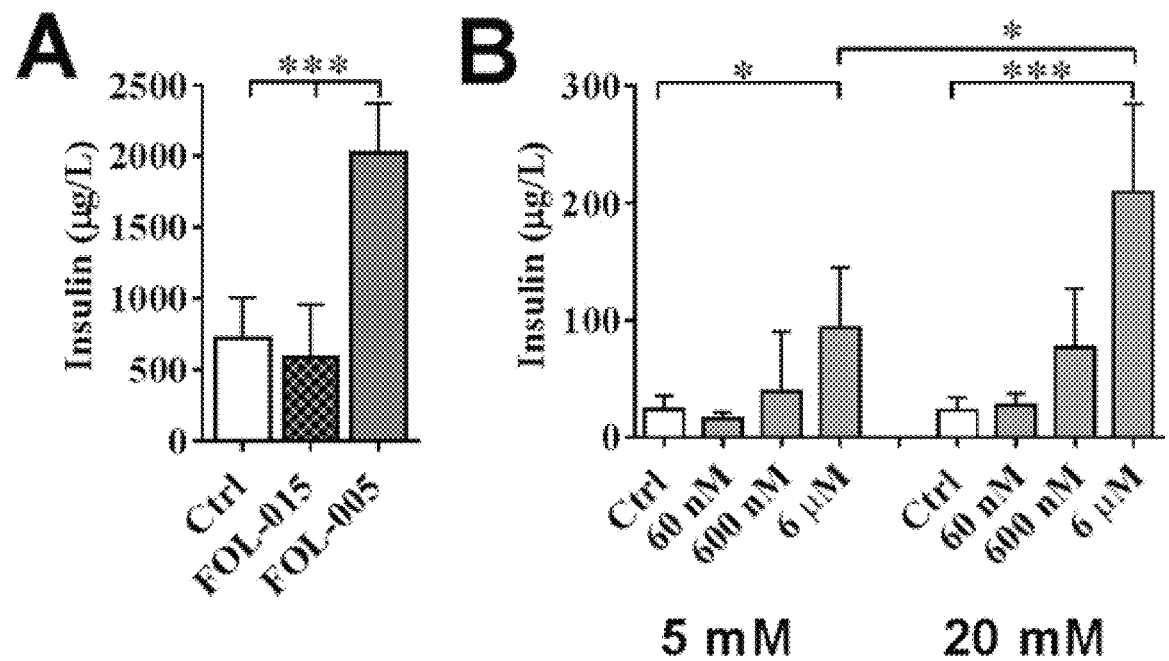
Figure 3:
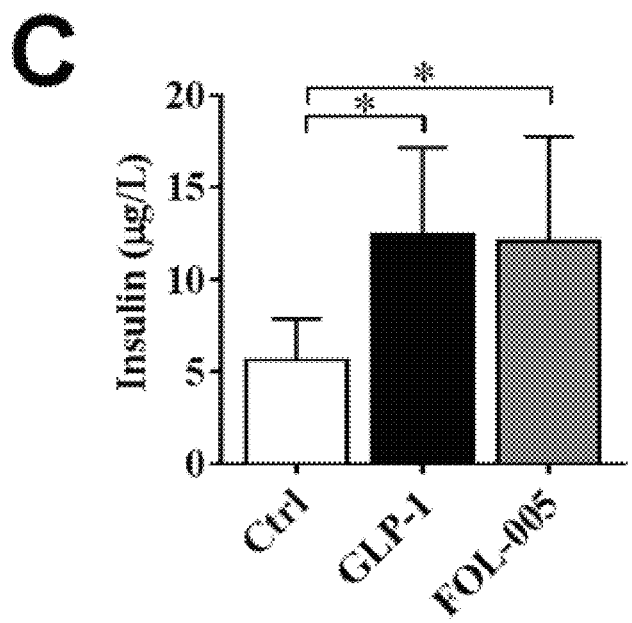

FIG. 3. Insulin secretion was increased from islets and β-cells following FOL-005 stimulation FOL-005 stimulated β-cell and islet insulin secretion. Insulin release from INS-1 cells was increased after FOL-005 (6 μM) stimulation in-non glucose containing media compared to non-stimulated control (ctrl) and to a scrambled control peptide (FOL-015) (FIG. 3A). FOL-005 stimulated insulin release from INS-1 at both low (5 mM) and high (20 mM) glucose (FIG. 3B). Isolated mouse pancreatic islets stimulated with FOL-005 (6 μM) or GLP-1 (100 nM) secreted more insulin compared to unstimulated control islets (FIG. 3C). Mean±SD are presented for 5-6 different observations in each group.

Figure 4:
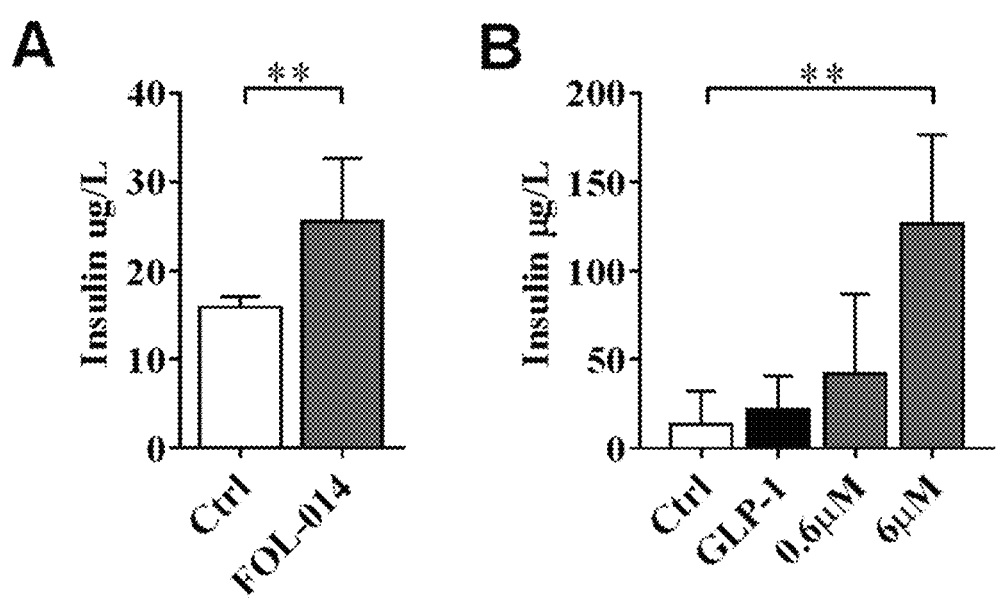

FIG. 4. Insulin secretion was increased from islets and β-cells following FOL-014 stimulation FOL-014 stimulated insulin secretion from β-cells and pancreatic islets. INS-1 cells stimulated with FOL-014 (6 μM) secreted more insulin compared to unstimulated control cells (FIG. 4A). Isolated mouse pancreatic islets stimulated with FOL-014 (6 μM) secreted more insulin compared to control islets (FIG. 4B). Addition of GLP-1 (100 nM) or FOL-014 (0.6 μM) had no effect on insulin secretion. Mean±SD are presented for 5-6 different observations in each group.

Figure 5:
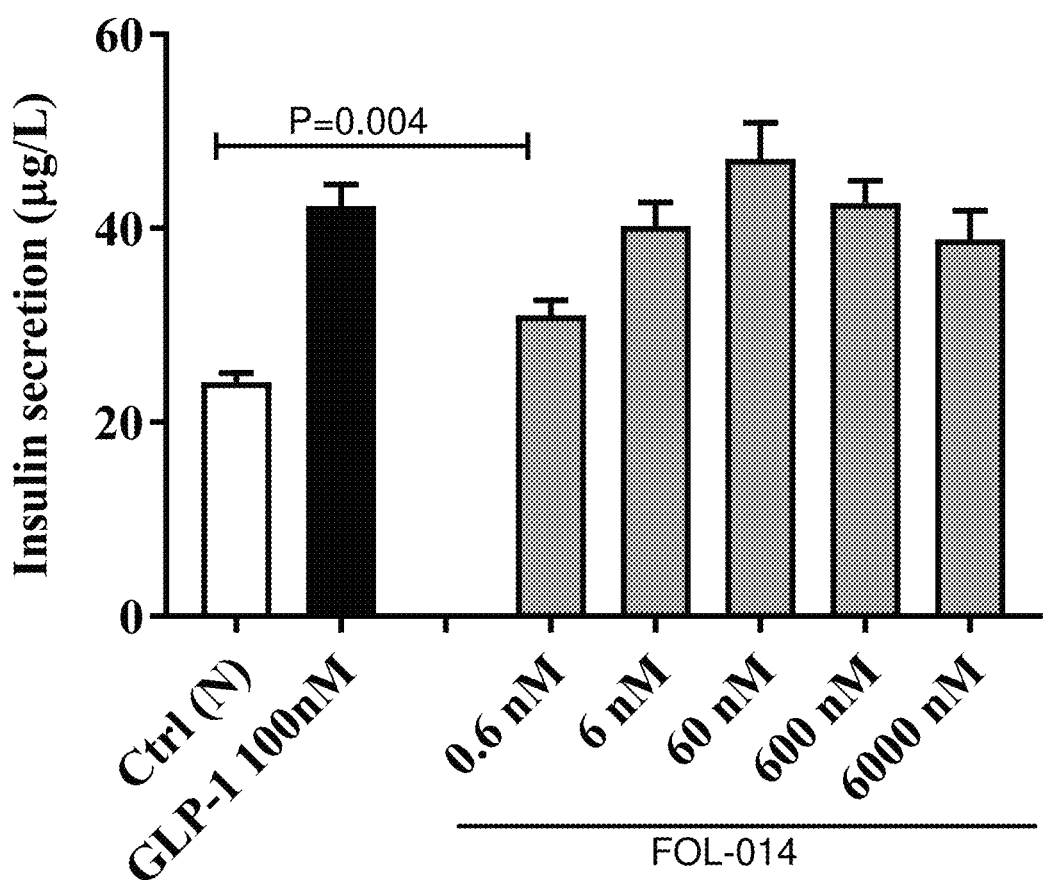

FIG. 5. The effect of FOL-014 on insulin secretion was dose dependent. Stimulation of INS-1 cells by increasing doses of FOL-014 resulted in a significant increase in insulin secretion for all concentrations tested. The insulin secretion increased in a linear fashion in the presence of FOL-014 ranging from 0.6 nM to 60 nM. Higher concentrations appeared to result in a less pronounced effect on insulin secretion. Furthermore, FOL-014 induced insulin secretion was comparable to the effect of 100 nM GLP-1. Bars represent mean values and standard error of the mean (SEM).

Figure 6:
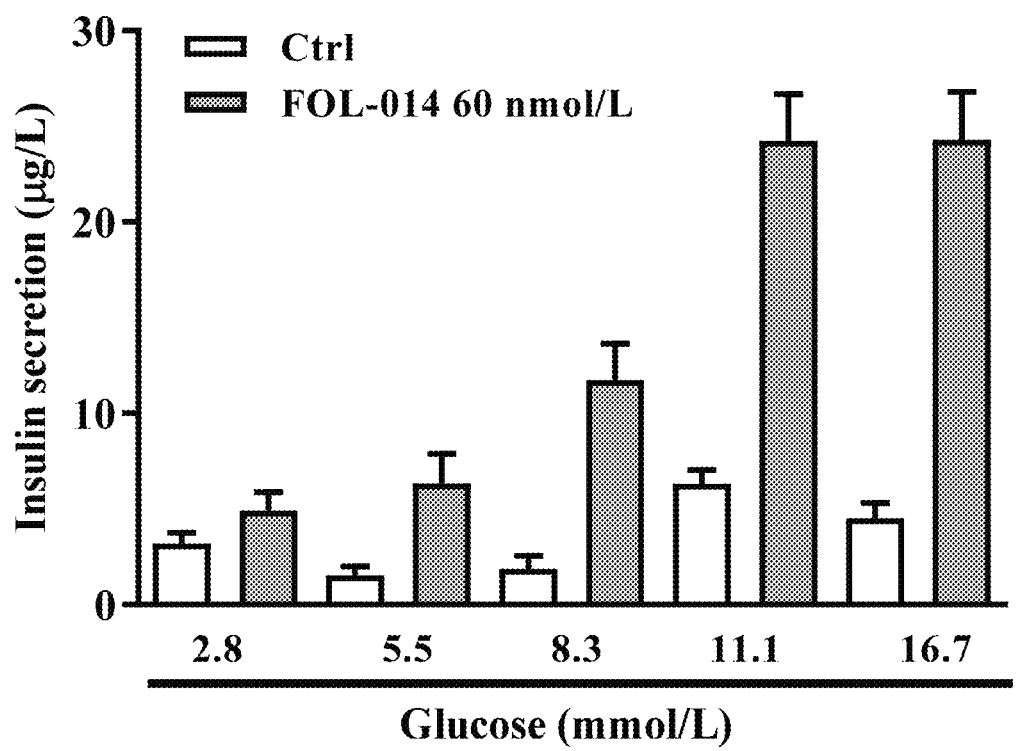

FIG. 6. The effect on insulin secretion of FOL-014 was glucose concentration dependent. The insulin secretion from untreated or FOL-014 exposed INS-1 cells was measured in the presence of increasing glucose concentrations. At glucose levels 5.5 mM or higher, the insulin secretion was significantly higher in the FOL-014 treated cells, as compared to untreated control cells. Bars represent mean values and standard error of the mean (SEM).

Figure 7:
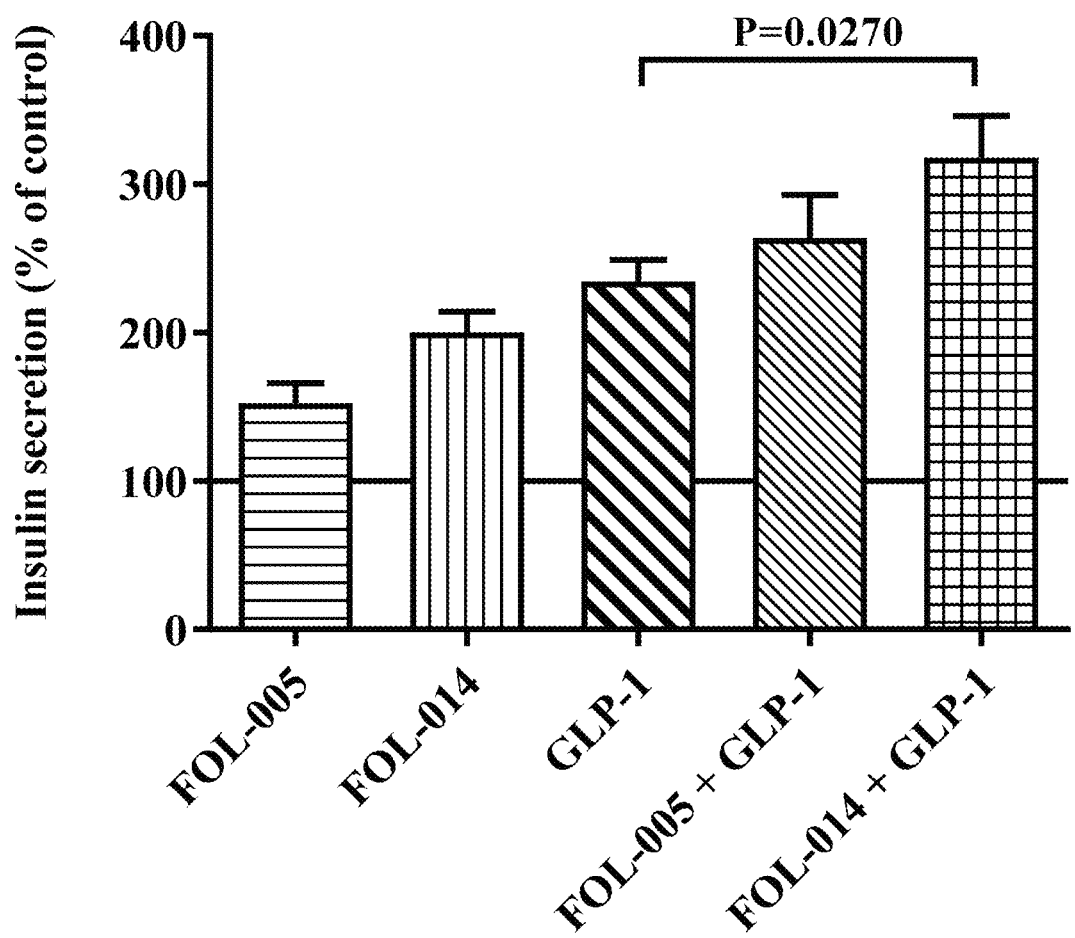

FIG. 7. FOL-005 and FOL-014 dosed together with native GLP-1 elicited an additive effect on insulin secretion. The insulin release from INS-1 cells was measured following combination treatment of GLP-1 together with FOL-005 and FOL-014 (all three peptides in a concentration of 100 nM), respectively and compared with the effect of each peptide alone. The combination of GLP-1 and FOL-014 significantly increased the insulin secretion as compared with each peptide alone. An increase was also observed for the combination of FOL-005 and GLP-1. Bars represent mean values and standard error of the mean (SEM).

Figure 8:
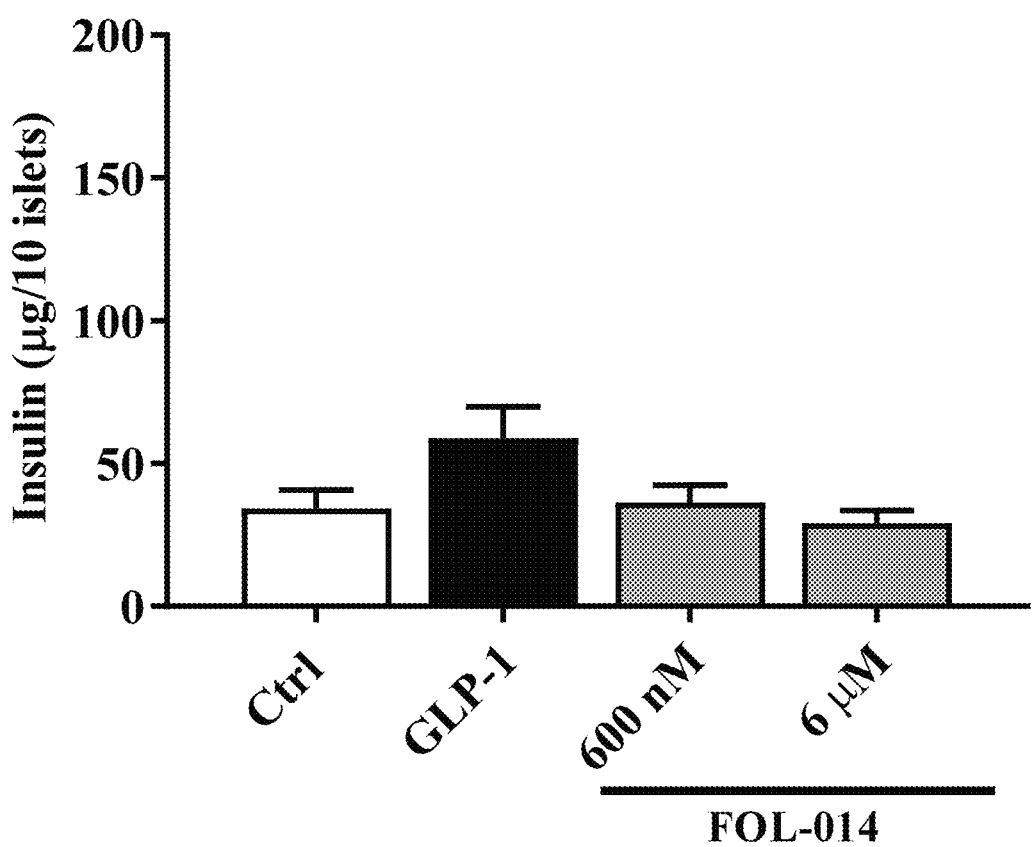

FIG. 8. FOL-014 affected insulin and glucagon secretion in pancreatic islets. Two different concentrations of FOL-014 were tested and compared with the effect of 100 nM GLP-1 on isolated mouse islets in low (2.8 mM) (A, C) and high (16.7 mM) (B, D) concentrations of glucose. In the low glucose samples, the presence of FOL-014 did not increase insulin secretion, but reduced glucagon secretion as compared with control and GLP-1. In the high glucose samples, 600 nM FOL-014 and GLP-1, but not 6 μM FOL-014, significantly increased insulin secretion (B), and GLP-1 as well as both concentrations of FOL-014 efficiently reduced glucagon secretion (D). Bars represent mean values and standard error of the mean (SEM).

Figure 9:
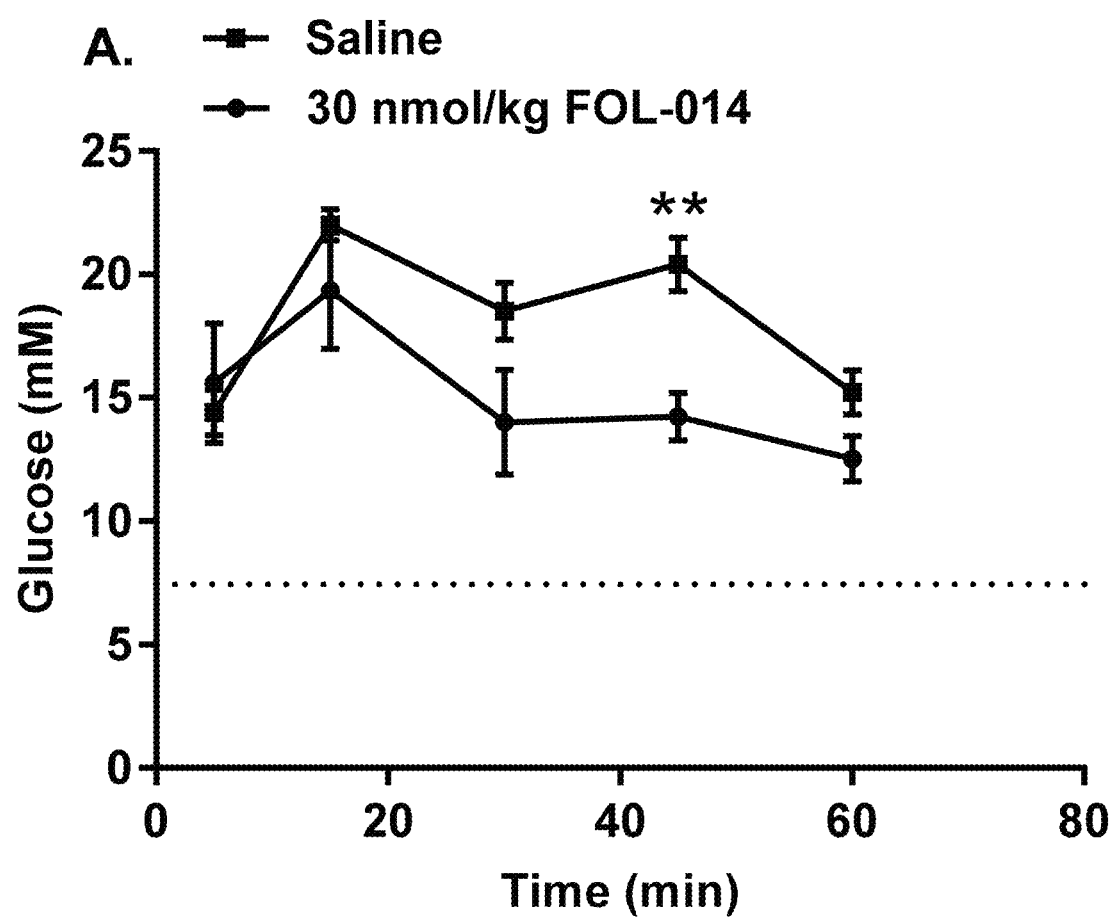

FIG. 9. FOL-014 lowered plasma glucose levels in vivo following a glucose injection. An intraperitoneal glucose tolerance test (IPGTT) was performed on wild type C57bl/6 mice. FOL-014 dosed at 200 nmol/kg significantly lowered the plasma glucose levels as compared to the control at 15 minutes, 30 minutes and 45 minutes (P=0.0027). At the 30 nmol/kg dose, FOL-014 lowered the glucose levels with a significant effect at 45 minutes after the glucose injection. The dotted line corresponds to mean non-fasting glucose levels. Data represents mean values and standard error of the mean (SEM). Statistical analysis was performed using student's t-test.

FIG. 10. FOL-014 delayed the onset of type-1 diabetes in BB lyp/lyp rats. BB lyp/lyp rats treated with FOL-014 showed a significant delay in the onset of diabetes defined as plasma glucose <11.1 mmol/l. Age of onset of diabetes for each rat was depicted in (A) with a significant difference between untreated and treated groups. The percentage of animals developing type 1 diabetes each day was depicted in (B) with a significant difference between groups. Error bars in (A) represent standard error of the mean (SEM).

Figure 11:
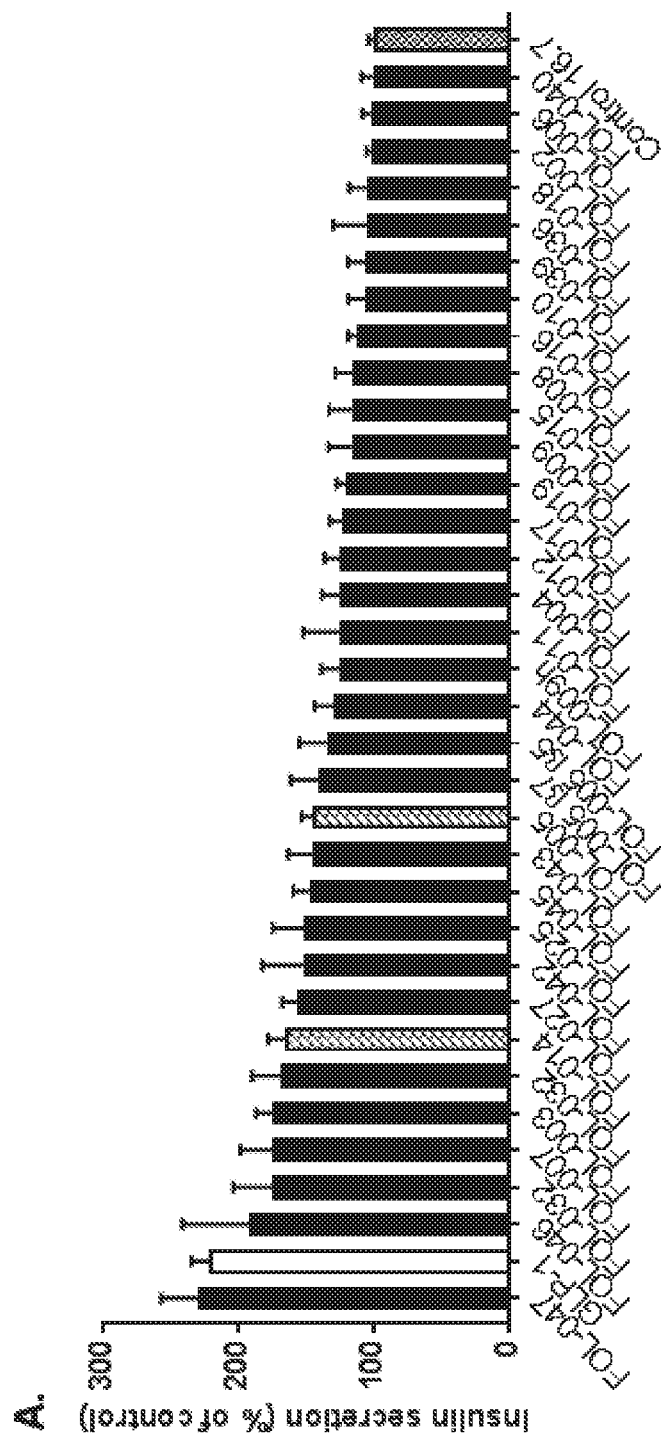

FIG. 11. The effect on insulin secretion of peptide analogues derived from FOL-005 or FOL-014. Novel peptide analogues were tested in two separate INS-1 cell lines (A and B) for their ability to induce insulin secretion under high glucose (16.7 mM) conditions. The effect was compared with that of native GLP-1, FOL-005 and FOL-014 as well as the effect of high glucose alone. Analogues inducing insulin release below the average of the high glucose control were considered non-functional (not shown). The level of insulin secretion is depicted in black, filled bars for the novel analogues, and in contrasting patterns for the comparators. Bars represent mean values and standard error of the mean (SEM).

Figure 12:
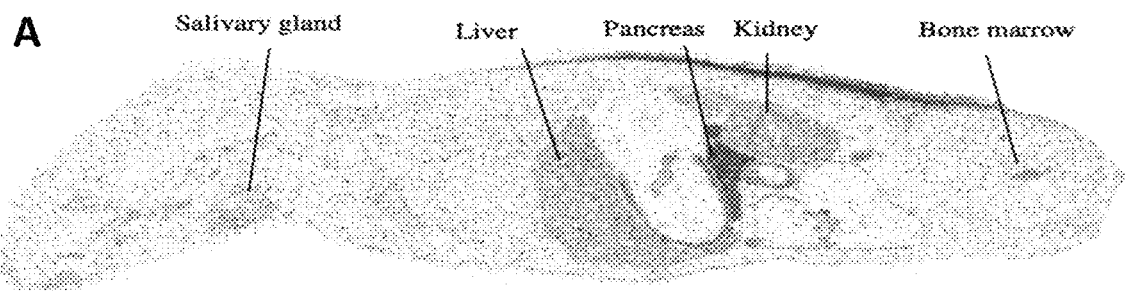
Figure 12:
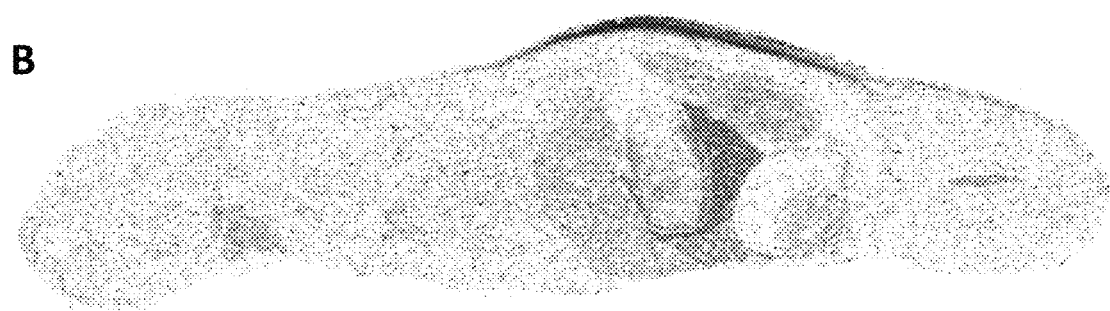
Figure 12:
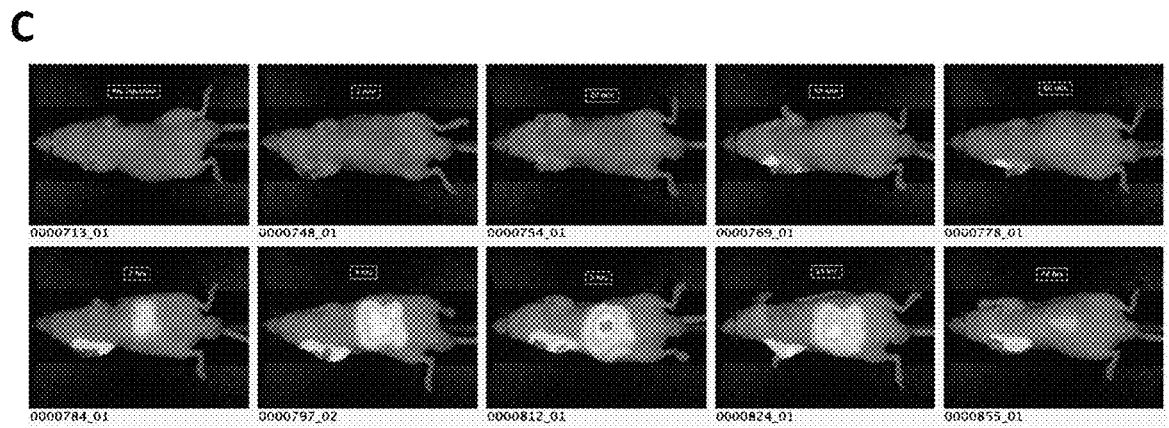
Figure 12:
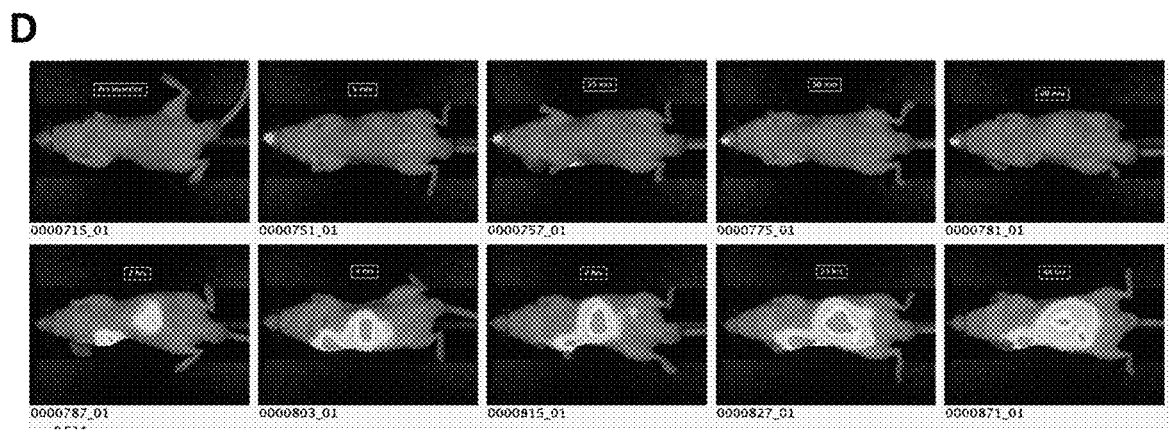

FIG. 12. FOL-005 and FOL-014 displayed specific distribution patterns following injection in mouse. Following subcutaneous administration of $^3$H-FOL-005, the highest overall levels of radioactivity were present in pancreas and at the injection site, 1 hour (A) and 2 hours (B) after injection. Accumulation of the $^3$H-FOL-005 is also visible in liver, kidney, salivary glands. Using Pearl Trilogy Small Animal Imaging System in vivo bio-distribution and tissue localization of Cy7.5 labelled FOL-005 (C) and FOL-014 (D) in NMRI nude mice via subcutaneous injection was investigated. Following initial control imaging, a dose of 10 nmol per mouse was administered and live imaging was performed at 5 min, 20 min, 50 min, 60 min, 2 hrs, 4 hrs, 6 hrs, 24 hrs and 48 hrs. High accumulation of both peptides was evident in the pancreatic region as well as at the injection site.

DETAILED DESCRIPTION

The disclosure is as defined in the claims.

In one aspect, the present disclosure concerns a peptide or a peptide analog comprising an amino acid sequence of the general formula:

a)
(SEQ ID NO: 140)
$$KX_2LAX_5X_6X_7X_8IX_{10}LX_{12}YGIK$$

wherein:
$X_2$ is C, P or G;
$X_5$ is E or G;
$X_6$ is C, D or I;
$X_7$ is D, I, S or G;
$X_8$ is S, D or G;
$X_{10}$ is E or G;
$X_{12}$ is S or T;
with the proviso that if $X_{12}$ is T, the peptide comprises no more than 25 amino acids; and
with the proviso that if $X_2$ is P, $X_5$ is E, $X_6$ is I, $X_7$ is D, $X_8$ is S, $X_{10}$ is E and $X_{12}$ is S, the peptide comprises no more than 85 amino acid residues;
b) a polynucleotide encoding upon expression, the peptide of a);
c) a vector comprising the polynucleotide of b); and
d) a cell comprising the polynucleotide of b), or the vector of c).

In one embodiment, the present disclosure concerns a peptide or a peptide analog comprising an amino acid sequence of the general formula:

(SEQ ID NO: 162)
$$KX_2LAX_5X_6X_7X_8IX_{10}LSYGIK$$

wherein:
$X_2$ is C, P or G;
$X_5$ is E or G;
$X_6$ is C, I or absent;
$X_7$ is D, G or absent;
$X_8$ is S, G or absent;
$X_{10}$ is E or G;
wherein absent means that the amino acid $X_5$ is coupled to the amino acid $X_{10}$ In one embodiment, the present disclosure concerns a peptide comprising an amino acid sequence of the general formula:

$$KX_2LAX_5IX_{10}LSYGIK \quad \text{(SEQ ID NO: 163)}$$

wherein:
$X_2$ is C, P or G;
$X_5$ is E or G;
$X_{10}$ is E or G.

In one embodiment, the present disclosure concerns an agent comprising:
a) a peptide, wherein the peptide is selected from the group consisting of:
  i) a peptide comprising or consisting of the amino acid sequence of SEQ ID NO: 136, 141, 142, 143, 144, 145, 146, 147, 148, 149, 150, 151, 152, 153, 154, 155, and 156;
  ii) a biologically active sequence variant of any one of the peptides of i), wherein any one amino acid has been altered for another proteinogenic or non-proteinogenic amino acid, with the proviso that no more than five amino acids are so altered;
  iii) a biologically active fragment of the peptide of any one of i) or ii), wherein the fragment comprises at least 10 consecutive amino acids of any one of i) or ii);
b) a polynucleotide encoding upon expression, the peptide of a);
c) a vector comprising the polynucleotide of b); and
d) a cell comprising the polynucleotide of b), or the vector of c).

In one embodiment, the present disclosure concerns an agent comprising:
a) a peptide, wherein the peptide comprises or consists of an amino acid sequence selected from the group consisting of GDPNDGRGDSVVYGLR (SEQ ID NO: 137), VDTYDGGISVVYGLR (SEQ ID NO: 138), and VDTYDGDGSVVYGLR (SEQ ID NO: 139). VDVPEGDISLAYGLR (SEQ ID NO: 157), LDG-LVRAYDNISPVG (SEQ ID NO: 158), GDPNGDIS-VVYGLR (SEQ ID NO: 159), VDVPNGDISLAYRLR (SEQ ID NO: 160) VDVPEGDISLAYRLR (SEQ ID NO: 161);
b) a polynucleotide encoding upon expression, the peptide of a);
c) a vector comprising the polynucleotide of b); and
d) a cell comprising the polynucleotide of b), or the vector of c).

In one embodiment, the present disclosure concerns a peptide comprising an amino acid sequence of the general formula:

$$VDVPZ_5GDISLAYZ_{13}LR \quad \text{(SEQ ID NO: 164)}$$

wherein:
$Z_5$ is E or N;
$Z_{13}$ is R or G.

In one embodiment, the present disclosure concerns a peptide comprising an amino acid sequence of the general formula:

$$VDTYDGZ_7Z_8SVVYGLR \quad \text{(SEQ ID NO: 165)}$$

wherein:
$Z_7$ is D or G;
$Z_8$ is I or G.

In one embodiment, the present disclosure concerns a peptide comprising an amino acid sequence of the general formula:

$$GDPNZ_5Z_6Z_7Z_8Z_9SVVYGLR \quad \text{(SEQ ID NO: 166)}$$

wherein:
$Z_5$ is D or G;
$Z_6$ is D or G
$Z_7$ is I or R;
$Z_8$ is G or absent;
$Z_9$ is D or absent.

The term 'absent' as used herein, e.g. "$X_6$ is C, I or absent" is to be understood as that the amino acid residues directly adjacent to the absent amino acid are directly linked to each other by a conventional amide bond.

The term "peptide analog" described herein refers to a peptide comprising or consisting of a non-naturally occurring peptide.

The term 'amino acid' as used herein includes the standard twenty genetically-encoded amino acids and their corresponding stereoisomers in the 'D' form (as compared to the natural 'L' form), omega-amino acids and other naturally-occurring amino acids, unconventional amino acids (e.g., α,α-disubstituted amino acids, N-alkyl amino acids, etc.) and chemically derivatized amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for peptides of the present disclosure, as long as the desired functional property is retained by the peptide. For the peptides shown, each encoded amino acid residue, where appropriate, is represented by a single letter designation, corresponding to the trivial name of the conventional amino acid.

Chemical derivatives of one or more amino acids may be achieved by reaction with a functional side group. Such derivatives include, for example, those molecules in which free amino groups have been derivatized to form amine hydrochlorides, p-toluene sulphonyl groups, carboxybenzoxy groups, t-butyloxycarbonyl groups, chloroacetyl groups or formyl groups. Free carboxyl groups may be derivatized to form salts, methyl and ethyl esters or other types of esters and hydrazides. Free hydroxyl groups may be derivatized to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

Some of the peptides of the disclosure shares amino acid sequence similarity with a sub-region of naturally occurring osteopontin proteins. In some embodiments, said peptide may be regarded as an active fragment of a naturally-occurring osteopontin protein or a variant of such as a fragment.

Some of the peptides of the disclosure shares amino acid sequence similarity with a sub-region of naturally occurring tenascin proteins. In some embodiments, said peptide may be regarded as an active fragment of a naturally-occurring tenascin protein or a variant of such as a fragment.

By "fragment", at least 5 contiguous amino acids of the amino acid sequence are included, for example at least 6, 7, 8, 9, 10, 11, 12, 13, 14 or 15 contiguous amino acids of the amino acid sequence. Thus, the fragment may be 15 or fewer amino acids in length, for example 14, 13, 12, 11, 10, 9, 8, 7, 6 or 5 amino acids in length In one embodiment, said peptide is of no more than no more than 85, such as no more than 80, such as no more than 75, such as no more than 70, such as no more than 65, such as no more than 60, such as nor more than 55, such as no more than 50, such as no more than 55, such as no more than 40 amino acids, such as no more than 35, such as no more than 30, such as no more than 28, such as no more than 26, such as no more than 24, such as no more than 22, such as no more than 20, such as no more than 19, such as no more than 18, such as no more than 17, such as no more than 16, such as no more than 15, such as no more than 14, such as no more than 13, such as no more than 12, such as no more than 11, such as no more than 10 amino acids in length.

In another embodiment, said peptide is between 5 and 30 amino acids in length, such as between 5 and 20, such as between 8 and 20, such as between 8 and 16, such as between 10 and 15 amino acids in length.

In yet another embodiment, said fragment comprises 15 or fewer amino acids in length, such as fewer than 14 amino acids, such as fewer than 13 amino acids, such as fewer than 12 amino acids, such as fewer than 11 amino acids, such as fewer than 10 amino acids, such as fewer than 9 amino acids, such as fewer than 8 amino acids, such as fewer than 7 amino acids, such as fewer than 6 amino acids, such as fewer than 5 amino acids in length.

The term "variant" refers to a peptide that does not share 100% amino acid sequence identity with the parent peptide, i.e. one or more amino acids must be mutated. "Mutated" refers to altering an amino acid at a specified position in the parent peptide. For example, an amino acid at a specified position may be deleted, altered, substituted or may be the site of an insertion/addition of one or more amino acids. It will be appreciated by persons skilled in the art that the substitutions may be conservative or non-conservative.

In one embodiment, said peptide variant comprises or consists of a sequence wherein no more than five amino acids are altered for another proteinogenic or non-proteinogenic amino acid, such as no more than 4 amino acids, such as no more than 3 amino acids, such as no more than 2 amino acids, such as no more than 1 amino acid is altered. In one embodiment, one or more amino acids are conservatively substituted. "Conservatively substituted" refers to a substitution of one amino acid with another with similar properties (size, hydrophobicity, etc), such that the function of the peptide is not significantly altered. Thus, by "conservative substitutions" is intended combinations such as Gly, Ala; Val, Ile, Leu; Asp, Glu; Asn, Gln; Ser, Thr; Lys, Arg; and Phe, Tyr.

In another embodiment, said peptide comprises or consists of one or more additional amino acids, inserted at the N- and/or C-terminus and/or internally within the sequence. In one embodiment, at least 2 additional amino acids, such as at least 3, such as at least 4, such as at least 5, such as at least 6, such as at least 7, such as at least 8, such as at least 9, such as at least 10, such as at least 15 or such as at least 20 additional amino acids are inserted. The additional amino acids may be the amino acids from the corresponding positions of the wildtype human osteopontin (SEQ ID NO: 66) or from the corresponding positions of the wildtype murine osteopontin (SEQ ID NO: 134). The term "corresponding positions" of the wildtype osteopontin we mean that the additional amino acids are the same as those present in the equivalent position in the above wildtype osteopontin (if one imagines that the amino acid sequence of SEQ ID NO:1 replaces the sequence underlined in italics in SEQ ID NO:66

In another embodiment, the peptide is selected from the group consisting of SEQ ID NO: 1, 136, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 137, 138, 139, 141, 142, 143, 144, 145, 146, 147, 148, 149, 150, 151, 152, 153, 154, 155, 156, 157, 158, 159, 160, 161, 167, 168 and 169;

```
i. 15-amino acid peptides:
VDTYDGDISVVYGLR           SEQ ID NO: 1

VDTYDGDISVVYGLS           SEQ ID NO: 2 ii. 14-amino acid peptides:
VDTYDGDISVVYGL            SEQ ID NO: 3

DTYDGDISVVYGLR           SEQ ID NO: 4

TYDGDISVVYGLRS          SEQ ID NO: 5 iii. 13-amino acid peptides:
VDTYDGDISVVYG             SEQ ID NO: 6

DTYDGDISVVYGL            SEQ ID NO: 7

TYDGDISVVYGLR           SEQ ID NO: 8

YDGDISVVYGLRS          SEQ ID NO: 9 iv. 12-amino acid peptides:
VDTYDGDISVVY              SEQ ID NO: 10

DTYDGDISVVYG             SEQ ID NO: 11

TYDGDISVVYGL            SEQ ID NO: 12

YDGDISVVYGLR           SEQ ID NO: 13

DGDISVVYGLRS          SEQ ID NO: 14 v. 11-amino acid peptides:
VDTYDGDISVV               SEQ ID NO: 15

DTYDGDISVVY              SEQ ID NO: 16

TYDGDISVVYG             SEQ ID NO: 17

YDGDISVVYGL            SEQ ID NO: 18

DGDISVVYGLR           SEQ ID NO: 19

GDISVVYGLRS          SEQ ID NO: 20 vi. 10-amino acid peptides:
VDTYDGDISV                SEQ ID NO: 21

DTYDGDISVV               SEQ ID NO: 22

TYDGDISVVY              SEQ ID NO: 23
```

-continued

| | |
|---|---|
| YDG<u>DIS</u>VVYG | SEQ ID NO: 24 |
| DG<u>DIS</u>VVYGL | SEQ ID NO: 25 |
| G<u>DIS</u>VVYGLR | SEQ ID NO: 26 |
| <u>DIS</u>VVYGLRS | SEQ ID NO: 27 | vii. 9-amino acid peptides:

| | |
|---|---|
| VDTYDG<u>DIS</u> | SEQ ID NO: 28 |
| DTYDG<u>DISV</u> | SEQ ID NO: 29 |
| TYDG<u>DISV</u>V | SEQ ID NO: 30 |
| YDG<u>DIS</u>VVY | SEQ ID NO: 31 |
| DG<u>DIS</u>VVYG | SEQ ID NO: 32 |
| G<u>DIS</u>VVYGL | SEQ ID NO: 33 |
| <u>DIS</u>VVYGLR | SEQ ID NO: 34 |
| <u>IS</u>VVYGLRS | SEQ ID NO: 35 | viii. 8-amino acid peptides:

| | |
|---|---|
| VDTYDG<u>DI</u> | SEQ ID NO: 36 |
| DTYDG<u>DIS</u> | SEQ ID NO: 37 |
| TYDG<u>DISV</u> | SEQ ID NO: 38 |
| YDG<u>DIS</u>VV | SEQ ID NO: 39 |
| DG<u>DIS</u>VVY | SEQ ID NO: 40 |
| G<u>DIS</u>VVYG | SEQ ID NO: 41 |
| <u>DIS</u>VVYGL | SEQ ID NO: 42 |
| <u>IS</u>VVYGLR | SEQ ID NO: 43 | ix. 7-amino acid peptides:

| | |
|---|---|
| VDTYG<u>D</u> | SEQ ID NO: 44 |
| DTYDG<u>DI</u> | SEQ ID NO: 45 |
| TYDG<u>DIS</u> | SEQ ID NO: 46 |
| YDG<u>DISV</u> | SEQ ID NO: 47 |
| DG<u>DIS</u>VV | SEQ ID NO: 48 |
| G<u>DIS</u>VVY | SEQ ID NO: 49 |
| <u>DIS</u>VVYG | SEQ ID NO: 50 |
| <u>IS</u>VVYGL | SEQ ID NO: 51 | x. 6-amino acid peptides:

| | |
|---|---|
| DTYDG<u>D</u> | SEQ ID NO: 52 |
| TYDG<u>DI</u> | SEQ ID NO: 53 |
| YDG<u>DIS</u> | SEQ ID NO: 54 |
| DG<u>DISV</u> | SEQ ID NO: 55 |
| G<u>DIS</u>VV | SEQ ID NO: 56 |
| <u>DIS</u>VVY | SEQ ID NO: 57 |
| <u>IS</u>VVYG | SEQ ID NO: 58 | xi. 5-amino acid peptides:

| | |
|---|---|
| TYDG<u>D</u> | SEQ ID NO: 59 |
| YDG<u>DI</u> | SEQ ID NO: 60 |
| DG<u>DIS</u> | SEQ ID NO: 61 |
| G<u>DISV</u> | SEQ ID NO: 62 |
| <u>DIS</u>VV | SEQ ID NO: 63 |
| <u>IS</u>VVY | SEQ ID NO: 64 |
| <u>S</u>VVYG | SEQ ID NO: 65 | xii. 16-amino acid peptide:

| | |
|---|---|
| VDTYDGRGDSVVYGLR | SEQ ID NO: 67 | xiii. 15-amino acid peptides:

| | |
|---|---|
| VDVPNGDISLAYGLR | SEQ ID NO: 69 |
| DVPNGDISLAYGLRS | SEQ ID NO: 70 | xiv. 14-amino acid peptides:

| | |
|---|---|
| VDVPNG<u>DIS</u>LAYGL | SEQ ID NO: 71 |
| DVPNG<u>DIS</u>LAYGLR | SEQ ID NO: 72 |
| VPNG<u>DIS</u>LAYGLRS | SEQ ID NO: 73 | xv. 13-amino acid peptides:

| | |
|---|---|
| VDVPNG<u>DIS</u>LAYG | SEQ ID NO: 74 |
| DVPNG<u>DIS</u>LAYGL | SEQ ID NO: 75 |
| VPNG<u>DIS</u>LAYGLR | SEQ ID NO: 76 |
| PNG<u>DIS</u>LAYGLRS | SEQ ID NO: 77 | xvi. 12-amino acid peptides:

| | |
|---|---|
| VDVPNG<u>DIS</u>LAY | SEQ ID NO: 78 |
| DVPNG<u>DIS</u>LAYG | SEQ ID NO: 79 |
| VPNG<u>DIS</u>LAYGL | SEQ ID NO: 80 |
| PNG<u>DIS</u>LAYGLR | SEQ ID NO: 81 |
| NG<u>DIS</u>LAYGLRS | SEQ ID NO: 82 | xvii. 11-amino acid peptides:

| | |
|---|---|
| VDVPNG<u>DIS</u>LA | SEQ ID NO: 83 |
| DVPNG<u>DIS</u>LAY | SEQ ID NO: 84 |
| VPNG<u>DIS</u>LAYG | SEQ ID NO: 85 |
| PNG<u>DIS</u>LAYGL | SEQ ID NO: 86 |
| NG<u>DIS</u>LAYGLR | SEQ ID NO: 87 |
| G<u>DIS</u>LAYGLRS | SEQ ID NO: 88 | xviii. 10-amino acid peptides:

| | |
|---|---|
| VDVPNG<u>DIS</u>L | SEQ ID NO: 89 |
| DVPNG<u>DIS</u>LA | SEQ ID NO: 90 |
| VPNG<u>DIS</u>LAY | SEQ ID NO: 91 |
| PNG<u>DIS</u>LAYG | SEQ ID NO: 92 |
| NG<u>DIS</u>LAYGL | SEQ ID NO: 93 |
| G<u>DIS</u>LAYGLR | SEQ ID NO: 94 |
| <u>DIS</u>LAYGLRS | SEQ ID NO: 95 | xix. 9-amino acid peptides:

| | |
|---|---|
| VDVPNG<u>DIS</u> | SEQ ID NO: 96 |
| DVPNG<u>DISL</u> | SEQ ID NO: 97 |
| VPNG<u>DIS</u>LA | SEQ ID NO: 98 |
| PNG<u>DIS</u>LAY | SEQ ID NO: 99 |
| NG<u>DIS</u>LAYG | SEQ ID NO: 100 |

-continued

| GDISLAYGL | SEQ ID NO: 101 |
| DISLAYGLR | SEQ ID NO: 102 |
| ISLAYGLRS | SEQ ID NO: 103 | xx. 8-amino acid peptides:
| VDVPNGDI | SEQ ID NO: 104 |
| DVPNGDIS | SEQ ID NO: 105 |
| VPNGDISL | SEQ ID NO: 106 |
| PNGDISLA | SEQ ID NO: 107 |
| NGDISLAY | SEQ ID NO: 108 |
| GDISLAYG | SEQ ID NO: 109 |
| DISLAYGL | SEQ ID NO: 110 |
| ISLAYGLR | SEQ ID NO: 111 | xxi. 7-amino acid peptides:
| VDVPNGD | SEQ ID NO: 112 |
| DVPNGDI | SEQ ID NO: 113 |
| VPNGDIS | SEQ ID NO: 114 |
| PNGDISL | SEQ ID NO: 115 |
| NGDISLA | SEQ ID NO: 116 |
| GDISLAY | SEQ ID NO: 117 |
| DISLAYG | SEQ ID NO: 118 |
| ISLAYGL | SEQ ID NO: 119 | xxii. 6-amino acid peptides:
| DVPNGD | SEQ ID NO: 120 |
| VPNGDI | SEQ ID NO: 121 |
| PNGDIS | SEQ ID NO: 122 |
| NGDISL | SEQ ID NO: 123 |
| GDISLA | SEQ ID NO: 124 |
| DISLAY | SEQ ID NO: 125 |
| ISLAYG | SEQ ID NO: 126 | xxiii. 5-amino acid peptides:
| VPNGD | SEQ ID NO: 127 |
| PNGDI | SEQ ID NO: 128 |
| NGDIS | SEQ ID NO: 129 |
| GDISL | SEQ ID NO: 130 |
| DISLA | SEQ ID NO: 131 |
| ISLAY | SEQ ID NO: 132 |
| SLAYG | SEQ ID NO: 133 | xxiv. 16-amino acid peptides:
| KPLAEIDSIELSYGIK | SEQ ID NO: 136 |
| GDPNDGRGDSVVYGLR | SEQ ID NO: 137 | xxv. 15--amino acid peptides:
| VDTYDGGISVVYGLR | SEQ ID NO: 138 |
| VDTYDGDGSVVYGLR | SEQ ID NO: 139 | xxvi. 16-amino acid peptides:
| KCLAECDSIELSYGIK | SEQ ID NO: 141 | xxvii. 8--amino acid peptides:
| CLAEIDSC | SEQ ID NO: 142 | xxviii. 18-amino acid peptides:
| CFKPLAEIDSIECSYGIK | SEQ ID NO: 143 | xxix. 16--amino acid peptides:
| KPLAEDISIELSYGIK | SEQ ID NO: 144 |
| KPLAEISDIELSYGIK | SEQ ID NO: 145 |
| KPLAEIGDIELSYGIK | SEQ ID NO: 146 | xxx. 15-amino acid peptides:
| KPLAEGDIELSYGIK | SEQ ID NO: 147 | xxxi. 13--amino acid peptides:
| KPLAEIELSYGIK | SEQ ID NO: 148 | xxxii. 16--amino acid peptides:
| KPLAEIDSIELTYGIK | SEQ ID NO: 149 |
| KPLAEIDGIELSYGIK | SEQ ID NO: 150 |
| KPLAEIDGIELTYGIK | SEQ ID NO: 151 |
| KPLAEIGSIELSYGIK | SEQ ID NO: 152 |
| KGLAEIDSIELSYGIK | SEQ ID NO: 153 |
| KPLAGIDSIGLSYGIK | SEQ ID NO: 154 |
| KCLAEIDSCELSYGIK | SEQ ID NO: 155 | xxxiii. 13--amino acid peptides:
| CFKPLAEIDSIEC | SEQ ID NO: 156 | xxxiv. 15-amino acid peptides:
| VDVPEGDISLAYGLR | SEQ ID NO: 157 |
| LDGLVRAYDNISPVG | SEQ ID NO: 158 | xxxv. 14-amino acid peptides:
| GDPNGDISVVYGLR | SEQ ID NO: 159 | xxxvi. 15-amino acid peptides:
| VDVPNGDISLAYRLR | SEQ ID NO: 160 |
| VDVPEGDISLAYRLR | SEQ ID NO: 161 |
| V(beta-D)TYDGDISVVYGLR | SEQ ID NO: 167 |
| VDTY(beta-D)GDISVVYGLR | SEQ ID NO: 168 |
| VDTYDG(beta-D)ISVVYGLR | SEQ ID NO: 169 |

In one embodiment said peptide is derived from osteopontin, such as a mammalian osteopontin variant and/or fragment.

In one embodiment, said peptide is non-naturally occurring, such as a peptide comprising non-proteinogenic amino acid residues.

In some embodiments, said peptide is further conjugated to a moiety, which may be selected from the group consisting of PEG, monosaccharides, fluorophores, chromophores, radioactive compounds, and cell-penetrating peptides. In one embodiment, the fluorophore is selected from the group consisting of *Lucifer* yellow, biotin, 5,6-carboxyltetramethylrhodamine (TAMRA), indodicarbocyanine (C5) Alexa Fluor@ 488, Alexa Fluor@ 532, Alexa Fluor@ 647, ATTO 488, ATTO 532, 6-carboxyfluorescein (6-FAM), Alexa Fluor@ 350, DY-415, ATTO 425, ATTO 465, Bodipy® FL, fluorescein isothiocyanate, Oregon Green@ 488, Oregon Green@ 514, Rhodamine Green™, 5'-Tetrachloro-Fluorescein, ATTO 520, 6-carboxy-4',5'-dichloro-2',7'-dimethoxy-fluoresceine, Yakima Yellow™ dyes, Bodipy® 530/550, hexachloro-fluorescein, Alexa Fluor@ 555, DY-549, Bodipy® TMR-X, cyanine phosphoramidites (cyanine 3, cyanine 3.5, cyanine 5, cyanine 5.5, cyanine 7.5), ATTO 550, Rhodamine Red™, ATTO 565, Carboxy-X-Rhodamine, Texas Red (Sulforhodamine 101 acid chloride), LightCycler@ Red 610, ATTO 594, DY-480-XL, DY-610, ATTO 610, LightCycler@ Red 640, Bodipy 630/650, ATTO 633, Bodipy 650/665, ATTO 647N, DY-649, LightCycler@ Red 670, ATTO 680, LightCycler@ Red 705, DY-682, ATTO 700, ATTO 740, DY-782, IRD 700, IRD 800, CAL Fluor@ Gold 540 nm, CAL Fluor@ Gold 522 nm, CAL Fluor@ Gold 544 nm, CAL Fluor@ Orange 560 nm, CAL Fluor@ Orange 538 nm, CAL Fluor@ Orange 559 nm, CAL Fluor@ Red 590 nm, CAL Fluor@ Red 569 nm, CAL Fluor@ Red 591 nm, CAL Fluor@ Red 610 nm, CAL Fluor@ Red 590 nm, CAL Fluor@ Red 610 nm, CAL Fluor@ Red 635 nm, Quasar@ 570 nm, Quasar@ 548 nm, Quasar@ 566 nm (Cy 3), Quasar@ 670 nm, Quasar@ 647 nm, Quasar@ 670 nm, Quasar@ 705 nm, Quasar@ 690 nm, Quasar@ 705 nm (Cy 5.5), Pulsar@ 650 Dyes, SuperRox® Dyes).

In another embodiment, said peptide is further modified such as being glycosylated or by PEGylation, amidation, esterification, acylation, acetylation and/or alkylation.

In one embodiment, said peptide comprises or consists of tandem repeats, which may comprise or consist of the amino acid sequence of any one or more of the sequences as described herein.

In one embodiment, said peptide is cyclic. The cyclic structure may be achieved by any suitable method of synthesis. Thus, heterodetic linkages may include, but are not limited to formation via disulphide, cysteine, alkylene or sulphide bridges.

In a further embodiment, the peptide comprises or consists of a fusion. For example, the peptide may comprise a fusion of the amino acid sequence of SEQ ID NO: 1 or 136.

The term 'fusion' of a peptide relates to an amino acid sequence corresponding to, for example, SEQ ID NO: 1 or 136 (or a fragment or variant thereof) fused to any other peptide. For example, the said peptide may be fused to a polypeptide such as glutathione-S-transferase (GST) or protein A in order to facilitate purification of said peptide. Examples of such fusions are well known to those skilled in the art. Similarly, the said peptide may be fused to an oligo-histidine tag such as His6 or to an epitope recognised by an antibody such as the well-known Myc tag epitope. Fusions to any variant or derivative of said peptide are also included in the scope of the disclosure.

Alternatively, the fused portion may be a lipophilic molecule or peptide domain that is capable of promoting cellular uptake of the polypeptide, as known to those skilled in the art.

Novel Peptides

In one embodiment, the present disclosure relates to a peptide comprising or consisting of an amino acid sequence selected from the group consisting of KPLAEIDSIELSYGIK (SEQ ID NO: 136), GDPNDGRGDSVVYGLR (SEQ ID NO: 137), VDTYDGGISVVYGLR (SEQ ID NO: 138), and VDTYDGDGSVVYGLR (SEQ ID NO: 139), VDVPEGDISLAYGLR (SEQ ID NO: 157), LDGLVRAYDNISPVG (SEQ ID NO: 158), GDPNGDISVVYGLR (SEQ ID NO: 159), VDVPNGDISLAYRLR (SEQ ID NO: 160) VDVPEGDISLAYRLR (SEQ ID NO: 161), or a variant or fragment thereof.

In another embodiment, the present disclosure relates to a peptide comprising or consisting of an amino acid sequence selected from the group consisting of KCLAECDSIELSYGIK (SEQ ID NO: 141), CLAEIDSC (SEQ ID NO: 142), CFKPLAEIDSIECSYGIK (SEQ ID NO: 143), KPLAEDISIELSYGIK (SEQ ID NO: 145), KPLAEIGDIELSYGIK (SEQ ID NO: 146), KPLAEGDIELSYGIK (SEQ ID NO: 147), KPLAEIELSYGIK (SEQ ID NO: 148), KPLAEIDSIELTYGIK (SEQ ID NO: 149), KPLAEIDGIELSYGIK (SEQ ID NO: 150), KPLAEIDGIELTYGIK (SEQ ID NO: 151), KPLAEIGSIELSYGIK (SEQ ID NO: 152), KGLAEIDSIELSYGIK (SEQ ID NO: 153), KPLAGIDSIGLSYGIK (SEQ ID NO: 154), KCLAEIDSCELSYGIK (SEQ ID NO: 155) and CFKPLAEIDSIEC (SEQ ID NO: 156), or a variant or fragment thereof.

In one embodiment, the present disclosure relates to the agent comprising a peptide, wherein the peptide comprises or consists of the amino acid sequence KPLAEIDSIELSYGIK (SEQ ID NO: 136), or a variant or fragment thereof.

In one embodiment, the present disclosure relates to the agent comprising a peptide, wherein the peptide comprises or consists of the amino acid sequence KPLAGIDSIGLSYGIK (SEQ ID NO: 154), or a variant or fragment thereof.

In one embodiment, the present disclosure relates to the agent comprising a peptide, wherein the peptide comprises or consists of the amino acid sequence KGLAEIDSIELSYGIK (SEQ ID NO: 153), or a variant or fragment thereof.

In one embodiment, the present disclosure relates to the agent comprising a peptide, wherein the peptide comprises or consists of the amino acid sequence KCLAECDSIELSYGIK (SEQ ID NO: 141), or a variant or fragment thereof.

In one embodiment, the present disclosure relates to the agent comprising a peptide, wherein the peptide comprises or consists of the amino acid sequence KPLAEIDGIELTYGIK (SEQ ID NO: 151), or a variant or fragment thereof.

In one embodiment, the present disclosure relates to the agent comprising a peptide, wherein the peptide comprises or consists of the amino acid sequence KPLAEIGSIELSYGIK (SEQ ID NO: 152), or a variant or fragment thereof.

In one embodiment, the present disclosure relates to the agent comprising a peptide, wherein the peptide comprises or consists of the amino acid sequence KPLAEIELSYGIK (SEQ ID NO: 148), or a variant or fragment thereof.

In one embodiment, the present disclosure relates to an agent comprising:
  b) a peptide or peptide analog comprising or consisting of the amino acid sequence GDPNDGRGDSVVYGLR (SEQ ID NO: 137), VDTYDGGISVVYGLR (SEQ ID NO: 138), and VDTYDGDGSVVYGLR (SEQ ID NO: 139). VDVPEGDISLAYGLR (SEQ ID NO: 157), LDGLVRAYDNISPVG (SEQ ID NO: 158), GDPNGDISVVYGLR (SEQ ID NO: 159), VDVPNGDISLAYRLR (SEQ ID NO: 160) VDVPEGDISLAYRLR (SEQ ID NO: 161), V(beta-D)TYDGDISVVYGLR (SEQ ID NO:167), VDTY(beta-D)GDISVVYGLR (SEQ ID NO: 168), VDTYDG(beta-D)ISVVYGLR (SEQ ID NO:169);
  b) a polynucleotide encoding upon expression, the peptide of a);
  c) a vector comprising the polynucleotide of b); and
  d) a cell comprising the polynucleotide of b), or the vector of c).

In some embodiments, said variant comprises or consists of a sequence wherein any one amino acid has been altered for another proteinogenic or non-proteinogenic amino acid, with the proviso that no more than five amino acids are so altered, such as no more than 4 amino acids, such as no more than 3 amino acids, such as no more than 2 amino acids, such as no more than 1 amino acid is altered. In some embodiments, one or more amino acids are conservatively substituted.

In some embodiments, said peptide comprises or consists of one or more additional amino acids, inserted at the N- and/or C-terminus and/or internally within the sequence. In one embodiment, at least 2 additional amino acids, such as at least 3, such as at least 4, such as at least 5, such as at least 6, such as at least 7, such as at least 8, such as at least 9, such as at least 10, such as at least 15 or such as at least 20 additional amino acids are inserted.

In some embodiments, said peptide is no more than 85, such as no more than 80, such as no more than 75, such as no more than 70, such as no more than 65, such as no more than 60, such as nor more than 55, such as no more than 50, such as no more than 55, such as no more than 40 amino acids, such as no more than 35, such as no more than 30, such as no more than 28, such as no more than 26, such as no more than 24, such as no more than 22, such as no more than 20, such as no more than 19, such as no more than 18, such as no more than 17, such as no more than 16, such as no more than 15, such as no more than 14, such as no more than 13, such as no more than 12, such as no more than 11, such as no more than 10 amino acids in length.

In some embodiments, said peptide is further conjugated to a moiety, which may be selected from the group consisting of PEG, monosaccharides, fluorophores, chromophores, radioactive compounds, and cell-penetrating peptides.

In one embodiment, said peptide is further modified such as being glycosylated or by PEGylation, amidation, esterification, acylation, acetylation and/or alkylation.

In some embodiments, said peptide comprises or consists of tandem repeats, which may comprise or consist of the amino acid sequence of any one or more of the sequences as described herein above.

In one embodiment, said peptide is cyclic. The cyclic structure may be achieved by any suitable method of synthesis. Thus, heterodetic linkages may include, but are not limited to formation via, cysteine, disulphide, alkylene or sulphide bridges.

Indications

The agents of the present disclosure are suitable for use in the treatment of endocrine, nutritional and metabolic diseases and disorders.

In one embodiment, the mammal in need of treatment of an endocrine disease, a nutritional disease and/or a metabolic disease is a human.

In some embodiments, the endocrine disease, nutritional disease and/or metabolic disease is selected from the group consisting of diabetes mellitus, type 1 diabetes mellitus, type 2 diabetes mellitus, malnutrition-related diabetes mellitus, disorders of glucose regulation and pancreatic internal secretion, insulin resistance syndrome, impaired glucose tolerance, hyperglycemia, hyperinsulinemia, and any combinations thereof.

In some embodiments, the endocrine disease, nutritional disease and/or metabolic disease is selected from the group consisting of diabetes mellitus, disorders of the thyroid gland, disorders of glucose regulation and pancreatic internal secretion, disorders of endocrine glands, malnutrition, nutritional deficiencies, obesity, hyperalimentation, and metabolic disorders.

In one embodiment, diabetes mellitus is selected from the group consisting of type 1 diabetes mellitus, type 2 diabetes mellitus, malnutrition-related diabetes mellitus, specified diabetes mellitus, and unspecified diabetes mellitus.

In one embodiment, disorders of glucose regulation and pancreatic internal secretion are selected from the group consisting of nondiabetic hypoglycaemic coma and disorders of pancreatic internal secretion.

In one embodiment, disorders of obesity and hyperalimentation are selected from the group consisting of localized adiposity, hyperalimentation, and sequelae of hyperalimentation.

In one embodiment, disorders of nutritional deficiencies are selected from the group consisting of disorders of aromatic amino-acid metabolism, disorders of branched-chain amino-acid metabolism and fatty-acid metabolism, disorders of amino-acid metabolism, lactose intolerance, disorders of carbohydrate metabolism, disorders of sphingolipid metabolism, disorders of lipid storage disorders, disorders of glycosaminoglycan metabolism, disorders of glycoprotein metabolism, disorders of lipoprotein metabolism, lipidaemias, disorders of purine and pyrimidine metabolism, disorders of porphyrin and bilirubin metabolism, disorders of mineral metabolism, cystic fibrosis, amyloidosis, volume depletion, disorders of fluid, electrolyte and acid-base balance, and postprocedural endocrine and metabolic disorders.

Compositions

In one aspect, the present disclosure relates to a composition comprising the agent described herein.

In one aspect, the present disclosure relates to an agent selected from the group consisting of:
a) a peptide or a peptide analog selected from the group consisting of
  (i) a peptide comprising or consisting of an amino acid sequence of the general formula:

$KX_2LAX_5X_6X_7X_8IX_{10}LX_{12}YGIK$     (SEQ ID NO: 140)

wherein:
  $X_2$ is C, P or G;
  $X_5$ is E or G;
  $X_6$ is C, D or I;
  $X_7$ is D, I, S or G;
  $X_8$ is S, D or G;
  $X_{10}$ is E or G;
  $X_{12}$ is S or T with the proviso that if $X_{12}$ is T, the peptide comprises no more than 25 amino acid residues; and
  (ii) a peptide comprising or consisting of an amino acid sequence of the general formula:

$VDZ_3Z_4Z_5GZ_7Z_8SZ_{10}Z_{11}YGLR$     (SEQ ID NO: 68)

wherein:
  $Z_3$ is T or V;
  $Z_4$ is Y or P;
  $Z_5$ is D or N;
  $Z_7$ is D or G;
  $Z_8$ is I or G;
  $Z_{10}$ is V or L;
  $Z_{11}$ is V or A; and
  (iii) a peptide comprising or consists of an amino acid sequence selected from the group consisting of KCLAECDSIELSYGIK (SEQ ID NO: 141), CLAEIDSC (SEQ ID NO: 142), CFKPLAEIDSIEC-SYGIK (SEQ ID NO: 143), KPLAEIELSYGIK (SEQ ID NO: 148), KCLAEIDSCELSYGIK (SEQ ID NO: 155) and CFKPLAEIDSIEC (SEQ ID NO: 156);

b) a polynucleotide encoding upon expression, the peptide of a);
c) a vector comprising the polynucleotide of b); and
d) a cell comprising the polynucleotide of b), or the vector of c);
for use in the treatment of an endocrine disease, a nutritional disease and/or a metabolic disease in a mammal.

In one aspect, the present disclosure relates to a composition for use in treatment of an endocrine disease, a nutritional disease and/or a metabolic disease, comprising an agent described herein. In one embodiment, said composition is a pharmaceutical composition.

In one embodiment, the agent further comprises a second active ingredient. Said second active ingredient may be selected from the group consisting of insulin, glucagon-like peptide-1 (GLP-1), biguanides, forskolin compounds, sulfonylurea, a dipeptidyl peptidase-4 (DPP4) inhibitor, an alpha-glucosidase inhibitor, a thiazolidinedione, a meglitidine and a sodium-glucose cotransporter-2 (SGLT2) inhibitor.

Other Methods

In one aspect, the present disclosure concerns a method of treating an endocrine disease, a nutritional disease and/or a metabolic disease, the method comprising administering an agent described herein to a subject in need thereof.

In one aspect, the present disclosure concerns the use of an agent for the manufacture of a medicament for use in treatment of an endocrine disease, a nutritional disease and/or a metabolic disease in a mammal.

In one aspect, the present disclosure concerns a polynucleotide encoding upon expression the peptide as described herein. In one aspect, the present disclosure concerns a vector comprising said polynucleotide encoding upon expression the peptide as described herein. In one aspect, the present disclosure concerns a cell comprising said polynucleotide or said vector encoding upon expression the peptide as described herein In one aspect, the present disclosure concerns a method for increasing insulin secretion, the method comprising administering a therapeutically effective amount of a peptide described herein, to an individual in need thereof. In one embodiment, said method is an in vitro method.

In one aspect, the present disclosure concerns a method for decreasing blood glucose levels, the method comprising administering a therapeutically effective amount of a peptide described herein, to an individual in need thereof. In one embodiment, said method is an in vitro method. In one embodiment, insulin secretion is increased. In another embodiment, cellular uptake of glucose is increased. In yet another embodiment, insulin production is increased. In another embodiment glucagon production is decreased.

In one aspect, the present disclosure concerns a method, e.g. an in vitro method, for improving β-cell morphology, the method comprising administering a therapeutically effective amount of a peptide described herein, to an individual in need thereof.

In one aspect, the present disclosure concerns a method for improving β-cell viability, the method comprising administering a therapeutically effective amount of a peptide described herein, to an individual in need thereof.

In one aspect, the present disclosure concerns a method for delaying onset of diabetes and diabetes associated disorders and disease, the method comprising administering a therapeutically effective amount of a peptide described herein, to an individual in need thereof.

In one embodiment of the present disclosure, the agent may further comprise a detectable moiety. For example, a detectable moiety may comprise or consist of a radioisotope, such as a radioisotope selected from the group consisting of $^{99m}$Tc, $^{111}$In, $^{67}$Ga, $^{68}$Ga, $^{72}$As, $^{89}$Zr, $^{123}$I and $^{201}$Tl. The binding moieties may thus be coupled to nanoparticles that have the capability of multi-imaging (for example, SPECT, PET, MRI, Optical, or Ultrasound). Alternatively, the detectable moiety may comprise or consist of a paramagnetic isotope, such as a paramagnetic isotope is selected from the group consisting of $^{157}$Gd, $^{55}$Mn, $^{162}$Dy, $^{52}$Cr and $^{56}$Fe.

In the case that the agent comprises a detectable moiety, then the detectable moiety may be detectable by an imaging technique such as SPECT, PET, MRI, optical or ultrasound imaging.

In one aspect, the present disclosure concerns the use of agent described herein for the preparation of a diagnostic composition for the diagnosis of a disease, disorder or damage of the pancreas in an individual.

Items

1. An agent comprising:
   a) a peptide, wherein the peptide or peptide analog comprises an amino acid sequence of the general formula:

$KX_2LAX_5X_6X_7X_8IX_{10}LX_{12}YGIK$    (SEQ ID NO: 140)

wherein:
   $X_2$ is C, P or G;
   $X_5$ is E or G;
   $X_6$ is C, D or I;
   $X_7$ is D, I, S or G;
   $X_8$ is S, D or G;
   $X_{10}$ is E or G;
   $X_{12}$ is S or T;
   with the proviso that if $X_{12}$ is T, the peptide comprises no more than 25 amino acid residues; and
   with the proviso that if $X_2$ is P, $X_5$ is E, $X_6$ is I, $X_7$ is D, $X_8$ is S, $X_{10}$ is E and $X_{12}$ is S, the peptide comprises no more than 85 amino acid residues;
   or a biologically active fragment and/or variant of SEQ ID NO: 140;
   b) a polynucleotide encoding upon expression, the peptide of a);
   c) a vector comprising the polynucleotide of b); and
   d) a cell comprising the polynucleotide of b), or the vector of c).

2. An agent comprising a peptide, wherein the peptide comprises an amino acid sequence of the general formula:

$VDVPZ_5GDISLAYZ_{13}LR$    (SEQ ID NO: 164)

wherein:
   $Z_5$ is E or N;
   $Z_{13}$ is R or G.

3. An agent comprising a peptide, wherein the peptide comprises an amino acid sequence of the general formula:

$VDTYDGZ_7Z_8SVVYGLR$    (SEQ ID NO: 165)

wherein:
   $Z_7$ is D or G;
   $Z_8$ is I or G.

4. An agent comprising a peptide, wherein the peptide comprises an amino acid sequence of the general formula:

$GDPNZ_5Z_6Z_7Z_8Z_9SVVYGLR$    (SEQ ID NO: 166)

wherein:
   $Z_5$ is D or G;
   $Z_6$ is D or G
   $Z_7$ is I or R;

$Z_8$ is G or absent;
$Z_9$ is D or absent.

5. The agent according to item 2 to 4, wherein the agent comprising:
   a) a peptide, wherein the peptide comprises or consists of an amino acid sequence selected from the group consisting of GDPNDGRGDSVVYGLR (SEQ ID NO: 137), VDTYDGGISVVYGLR (SEQ ID NO: 138), and VDTYDGDGSVVYGLR (SEQ ID NO: 139). VDVPEGDISLAYGLR (SEQ ID NO: 157), LDGLVRAYDNISPVG (SEQ ID NO: 158), GDPNGDISVVYGLR (SEQ ID NO: 159), VDVPNGDISLAYRLR (SEQ ID NO: 160) VDVPEGDISLAYRLR (SEQ ID NO: 161);
   b) a polynucleotide encoding upon expression, the peptide of a);
   c) a vector comprising the polynucleotide of b); and
   d) a cell comprising the polynucleotide of b), or the vector of c).

6. The agent according to item 1, wherein the peptide comprises or consists of an amino acid sequence of the general formula:

KX$_2$LAX$_5$X$_6$X$_7$X$_8$IX$_{10}$LSYGIK    (SEQ ID NO: 162)

wherein:
   $X_2$ is C, P or G;
   $X_6$ is C, I or absent;
   $X_7$ is D, G or absent;
   $X_8$ is S, G or absent;
   $X_{10}$ is E or G.

7. The agent according to item 6, wherein the peptide comprises an amino acid sequence of the general formula:

KX$_2$LAX$_5$IX$_{10}$LSYGIK    (SEQ ID NO: 163)

wherein:
   $X_2$ is C, P or G;
   $X_5$ is E or G;
   $X_{10}$ is E or G.

8. An agent comprising:
   a) a peptide or peptide analog comprising or consisting of the amino acid sequence GDPNDGRGDSVVYGLR (SEQ ID NO: 137), VDTYDGGISVVYGLR (SEQ ID NO: 138), and VDTYDGDGSVVYGLR (SEQ ID NO: 139). VDVPEGDISLAYGLR (SEQ ID NO: 157), LDGLVRAYDNISPVG (SEQ ID NO: 158), GDPNGDISVVYGLR (SEQ ID NO: 159), VDVPNGDISLAYRLR (SEQ ID NO: 160) VDVPEGDISLAYRLR (SEQ ID NO: 161), V(beta-D)TYDGDISVVYGLR (SEQ ID NO:167), VDTY(beta-D)GDISVVYGLR (SEQ ID NO: 168), VDTYDG(beta-D)ISVVYGLR (SEQ ID NO:169);
   b) a polynucleotide encoding upon expression, the peptide of a);
   c) a vector comprising the polynucleotide of b); and
   d) a cell comprising the polynucleotide of b), or the vector of c).

9. The agent according to any one of the preceding items, wherein the agent comprises non-naturally occurring, e.g. non-proteinogenic, amino acid residues.

10. The agent according to any one of the preceding items, wherein the agent is conjugated to a moiety.

11. The agent according to any one of the preceding items, wherein the moiety is selected from the group consisting of polyethylene glycol (PEG), monosaccharides, fluorophores, chromophores, radioactive compounds, and cell-penetrating peptides.

12. The agent according to any one of the preceding items, wherein the agent is further modified such as being glycosylated or by PEGylation, amidation, esterification, acylation, acetylation and/or alkylation.

13. The agent according to any one of the preceding items, wherein the agent comprises or consists of tandem repeats.

14. The agent according to any one of the preceding items, wherein the tandem repeats comprise or consist of the amino acid sequence of any one or more of the sequences as described in the preceding items.

15. The agent according to any of the preceding items, wherein the agent is fused to another polypeptide.

16. The agent according to any one of the preceding items, wherein the said polypeptide is selected from the group consisting of glutathione-S-transferase (GST) and protein A.

17. The agent according to any one of the preceding items, wherein the agent is fused to a tag.

18. The agent according to any one of the preceding items, wherein the said tag is an oligo-histidine tag.

19. The agent according to any one of the preceding items, wherein the agent is cyclic, such as wherein the peptide is cyclic.

20. The agent according to any one of the preceding items, wherein the peptide or peptide analog is capable of forming at least one intramolecular cysteine bridge, e.g. to form a cyclic or partially cyclic peptide.

21. The agent according to any one of the preceding items, wherein the peptide or peptide analog comprises or consists of an amino acid sequence selected from the group consisting of KCLAECDSIELSYGIK (SEQ ID NO: 141), CLAEIDSC (SEQ ID NO: 142), CFKPLAEIDSIECSYGIK (SEQ ID NO: 143), KPLAEDISIELSYGIK (SEQ ID NO: 145), KPLAEIGDIELSYGIK (SEQ ID NO: 146), KPLAEGDIELSYGIK (SEQ ID NO: 147), KPLAEIELSYGIK (SEQ ID NO: 148), KPLAEIDSIELTYGIK (SEQ ID NO: 149), KPLAEIDGIELSYGIK (SEQ ID NO: 150), KPLAEIDGIELTYGIK (SEQ ID NO: 151), KPLAEIGSIELSYGIK (SEQ ID NO: 152), KGLAEIDSIELSYGIK (SEQ ID NO: 153), KPLAGIDSIGLSYGIK (SEQ ID NO: 154), KCLAEIDSCELSYGIK (SEQ ID NO: 155) and CFKPLAEIDSIEC (SEQ ID NO: 156), or a variant or fragment thereof.

22. The agent according to any of the preceding items, wherein the peptide or peptide analog comprises or consists of the amino acid sequence KPLAEIDSIELSYGIK (SEQ ID NO: 136), or a variant or fragment thereof.

23. The agent according to any one of the preceding items, wherein the peptide or peptide analog comprises or consists of the amino acid sequence KPLAGIDSIGLSYGIK (SEQ ID NO: 154), or a variant or fragment thereof.

24. The agent according to any one of the preceding items, wherein the peptide or peptide analog comprises or consists of the amino acid sequence KGLAEIDSIELSYGIK (SEQ ID NO: 153), or a variant or fragment thereof.

25. The agent according to any one of the preceding items, wherein the peptide or peptide analog comprises or consists of the amino acid sequence KCLAECDSIELSYGIK (SEQ ID NO: 141), or a variant or fragment thereof.

26. The agent according to any one of the preceding items, wherein the peptide or peptide analog comprises or consists of the amino acid sequence KPLAEIDGIELTYGIK (SEQ ID NO: 151), or a variant or fragment thereof.

27. The agent according to any of the preceding items, wherein the peptide or peptide analog comprises or consists of the amino acid sequence KPLAEIGSIELSYGIK (SEQ ID NO: 152), or a variant or fragment thereof.

28. The agent according to any of the preceding items, wherein the peptide or peptide analog comprises or consists of the amino acid sequence KPLAEIELSYGIK (SEQ ID NO: 148), or a variant or fragment thereof.

29. The agent according to any one of the preceding items, wherein the variant comprises or consists of a sequence wherein any one amino acid has been altered for another proteinogenic or non-proteinogenic amino acid, with the proviso that no more than five amino acids are so altered.

30. The agent according to any one of the preceding items, wherein the variant comprises or consists of a sequence wherein no more than five amino acids are altered for another proteinogenic or non-proteinogenic amino acid, such as no more than 4 amino acids, such as no more than 3 amino acids, such as no more than 2 amino acids, such as no more than 1 amino acid is altered.

31. The agent according to any one of the preceding items, wherein one or more amino acids are conservatively substituted.

32. The agent according to any one of the preceding items, wherein the peptide or peptide analog comprises or consists of one or more additional amino acids, inserted at the N- and/or C-terminus and/or internally within the sequence.

33. The agent according to any one of the preceding items, wherein the peptide or peptide analog comprises 1 additional amino acid conjugated to either N- or C-terminal.

34. The agent according to any of the preceding items, wherein the agent comprises no more than 85, such as no more than 80, such as no more than 75, such as no more than 70, such as no more than 65, such as no more than 60, such as nor more than 55, such as no more than 50, such as no more than 55, such as no more than 40 amino acids, such as no more than 35, such as no more than 30, such as no more than 28, such as no more than 26, such as no more than 24, such as no more than 22, such as no more than 20, such as no more than 19, such as no more than 18, such as no more than 17, such as no more than 16, such as no more than 15, such as no more than 14, such as no more than 13, such as no more than 12, such as no more than 11, such as no more than 10 amino acids.

35. The agent according to any one of the preceding items, wherein the agent comprises at least 2 additional amino acids, such as at least 3, such as at least 4, such as at least 5, such as at least 6, such as at least 7, such as at least 8, such as at least 9, such as at least 10, such as at least 15 or such as at least 20 amino acids conjugated to the N- or C-terminus of the peptide.

36. The agent according to any of the preceding items, wherein the agent further comprises a detectable moiety.

37. The agent according to any of the preceding items, wherein the detectable moiety comprises or consists of a radioisotope.

38. The agent according to any of the preceding items, wherein the radioisotope is selected from the group consisting of $^{99m}$Tc, $^{111}$In, $^{67}$Ga, $^{68}$Ga, $^{72}$As, $^{89}$Zr, $^{123}$I and $^{201}$Tl.

39. The agent according to any of the preceding items, wherein the detectable moiety is detectable by an imaging technique such as SPECT, PET, MRI, optical or ultrasound imaging.

40. Use of the agent of any of the preceding items, for the preparation of a diagnostic composition for the diagnosis of a disease, disorder or damage of the pancreas in an individual.

41. A composition comprising the agent according to any of the preceding items.

42. The composition according to any one of the preceding items, wherein the composition is a pharmaceutical composition.

43. The agent or the composition according to any one of the preceding items, for use as a medicament.

44. An agent selected from the group consisting of:
    a) a peptide selected from the group consisting of
        (i) a peptide comprising or consisting of an amino acid sequence of the general formula:

KX$_2$LAX$_5$X$_6$X$_7$X$_8$IX$_{10}$LX$_{12}$YGIK           (SEQ ID NO: 140)

wherein:
            X$_2$ is C, P or G;
            X$_5$ is E or G;
            X$_6$ is C, D or I;
            X$_7$ is D, I, S or G;
            X$_8$ is S, D or G;
            X$_{10}$ is E or G;
            X$_{12}$ is S or T;
        with the proviso that if X$_{12}$ is T, the peptide comprises no more than 25 amino acid residues;
        or a biologically active fragment and/or variant of SEQ ID NO: 140;
        (ii) a peptide comprising or consisting of an amino acid sequence of the general formula:

VDZ$_3$Z$_4$Z$_5$GZ$_7$Z$_8$SZ$_{10}$Z$_{11}$YGLR           (SEQ ID NO: 68)

wherein:
            Z$_3$ is T or V;
            Z$_4$ is Y or P;
            Z$_5$ is D or N;
            Z$_7$ is D or G;
            Z$_8$ is I or G;
            Z$_{10}$ is V or L;
            Z$_{11}$ is V or A; and
    b) a polynucleotide encoding upon expression, the peptide of a);
    c) a vector comprising the polynucleotide of b); and
    d) a cell comprising the polynucleotide of b), or the vector of c);
    for use in the treatment of an endocrine disease, a nutritional disease and/or a metabolic disease in a mammal.

45. The agent or the composition for use according to item 44, wherein the peptide comprises or consists of an amino acid sequence selected from the group consisting of KCLAECDSIELSYGIK (SEQ ID NO: 141), CLAEIDSC (SEQ ID NO: 142), CFKPLAEIDSIECSYGIK (SEQ ID NO: 143), KPLAEIELSYGIK (SEQ ID NO: 148), KCLAEIDSCELSYGIK (SEQ ID NO: 155) and CFKPLAEIDSIEC (SEQ ID NO: 156);

46. The agent or the composition for use according to any one of the preceding items, wherein the peptide is selected from the group consisting of SEQ ID NO: 141, 142, 143, 144, 145, 146, 147, 148, 149, 150, 151, 152, 153, 154, 155 and 156.

47. The agent or the composition for use according to any one of the preceding items, wherein the peptide is selected from the group consisting of SEQ ID NO: 1, 136, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 67, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 135, 137, 138, 139, 157, 158, 159, 160, 161, 167, 168 and 169.
48. The agent or the composition for use according to any one of the preceding items, wherein said agent comprises a second or further active ingredient.
49. The agent or the composition for use according to item 48, wherein the second or further active ingredient is selected from the group consisting of insulin, glucagon-like peptide-1 (GLP-1), sulfonylurea, a dipeptidyl peptidase-4 (DPP4) inhibitor, an alpha-glucosidase inhibitor, a thiazolidinedione, a meglitidine and a sodium-glucose cotransporter-2 (SGLT2) inhibitor.
50. The agent or the composition according to any of the preceding items for use in the treatment of an endocrine disease, a nutritional disease and/or a metabolic disease in a mammal.
51. The agent or the composition for use according to item 50, wherein the mammal is a human.
52. The agent or the composition for use according to any one of the preceding items, wherein the endocrine disease, nutritional disease and/or metabolic disease are selected from the group consisting of diabetes mellitus, type 1 diabetes mellitus, type 2 diabetes mellitus, malnutrition-related diabetes mellitus, disorders of glucose regulation and pancreatic internal secretion, insulin resistance syndrome, impaired glucose tolerance, hyperglycemia, hyperinsulinemia, and any combinations thereof.
53. The agent or the composition for use according to any one of the preceding items, wherein the endocrine disease, nutritional disease and/or metabolic disease are selected from the group consisting of diabetes mellitus, disorders of the thyroid gland, disorders of glucose regulation and pancreatic internal secretion, disorders of endocrine glands, malnutrition, nutritional deficiencies, obesity, hyperalimentation, and metabolic disorders.
54. The agent or the composition for use according to any one of the preceding items, wherein the diabetes mellitus is selected from the group consisting of type 1 diabetes mellitus, type 2 diabetes mellitus, malnutrition-related diabetes mellitus, specified diabetes mellitus, and unspecified diabetes mellitus.
55. The agent or the composition for use according to any one of the preceding items, wherein the disorder of glucose regulation and pancreatic internal secretion is selected from the group consisting of nondiabetic hypoglycaemic coma and disorders of pancreatic internal secretion.
56. The agent or the composition for use according to any one of the preceding items, wherein the disorder of obesity and hyperalimentation is selected from the group consisting of localized adiposity, hyperalimentation, and sequelae of hyperalimentation.
57. The agent or the composition for use according to any one of the preceding items, wherein the disorder of nutritional deficiencies is selected from the group consisting of disorders of aromatic amino-acid metabolism, disorders of branched-chain amino-acid metabolism and fatty-acid metabolism, disorders of amino-acid metabolism, lactose intolerance, disorders of carbohydrate metabolism, disorders of sphingolipid metabolism, disorders of lipid storage disorders, disorders of glycosaminoglycan metabolism, disorders of glycoprotein metabolism, disorders of lipoprotein metabolism, lipiemias, disorders of purine and pyrimidine metabolism, disorders of porphyrin and bilirubin metabolism, disorders of mineral metabolism, cystic fibrosis, amyloidosis, volume depletion, disorders of fluid, electrolyte and acid-base balance, and postprocedural endocrine and metabolic disorders.
58. A method of treating an endocrine disease, a nutritional disease and/or a metabolic disease, the method comprising administering an agent according to any one of the preceding items to a subject in need thereof. 59. Use of an agent according to any one of the preceding items for the manufacture of a medicament for use in treatment of an endocrine disease, a nutritional disease and/or a metabolic disease in a mammal.
60. A method for delaying onset of diabetes and diabetes associated disorders and diseases, the method comprising administering a therapeutically effective amount of the agent as defined in any one of the preceding items, to an individual in need thereof.
61. A method for decreasing blood glucose levels, the method comprising administering a therapeutically effective amount of an agent of any one of the preceding items, to an individual in need thereof.
62. The method according to item 61, wherein insulin secretion is increased.
63. The method according to item 61, wherein cellular uptake of glucose is increased.
64. The method according to item 61, wherein the insulin production is increased. 65. The method according to item 61, wherein the glucagon production is decreased.
66. A method for improving beta cell viability, the method comprising administering a therapeutically effective amount of an agent of any one of the preceding items, to an individual in need thereof.
67. A method for improving beta cell morphology, the method comprising administering a therapeutically effective amount of an agent of any one of the preceding items, to an individual in need thereof.
68. A method for stabilising or improving viability and/or morphology of pancreatic islets, the method comprising administering a therapeutically effective amount of an agent of any one of the preceding items, to an individual in need thereof.

EXAMPLES

The disclosure is further illustrated by the following examples, which however should not be construed as being limiting for the disclosure. These examples demonstrate that exemplary peptides of the present disclosure stimulate β-cell proliferation, and have the ability to protect and rescue β-cells from apoptosis induced by glucotoxic conditions. It is also demonstrated that the exemplary peptides have the ability to stimulate insulin secretion from rat β-cells as well as isolated mouse pancreatic islets, where the peptides also are demonstrated to reduce glucagon levels. Furthermore, the examples demonstrate that the peptides reduce plasma glucose levels in vivo in a glucose tolerance test and that the peptides delay onset of type 1 diabetes in BB lyp/lyp rats Example 1: Peptide Design The novel peptides were designed following rational structure activity investigations. For FOL-005 (SEQ ID NO:

1) the peptides were designed around the RGD site but mutated in order to generate different structures that potentially could interact with different integrins. A sequence similar to FOL-005 was identified in the third fibronectin type III repeat domain (TNfn3) in tenascin-C and found to be reasonably similar to the mutated RGD site of FOL-005. A peptide was designed from this sequence denoted FOL-014. The X-ray crystal structure of the tenascin-3 TNfn3 domain (PDB code 1TEN, Leahy et al. (1992) Science 258(5084):987-91) was analyzed. The FOL-014 (SEQ ID NO: 136) sequence span the beta-turn before and the entire 3rd beta sheet. FOL-014 variants were designed to allow for structural modification and stabilization of the 3-dimensional molecular structure. Specifically, the peptides variants covered the beta-turn region with exposed side chains and some cyclized variants to maintain geometry.

All peptides were synthesized by solid phase peptide synthesis using several peptide manufacturers. Mainly, the peptide variants have been provided by Biopeptide Inc., California.

Example 2: FOL-005 and FOL-014 Induced Proliferation of INS-1 Cells

To investigate if FOL-005 and FOL-014 could induce proliferation of β-cells we used INS-1 cells. Rat INS-1 cells were seeded in 96-well plates in RPMI medium with supplement and after 2 hours the medium was changed to RPMI without supplement. During the proliferation experiment the cells were incubated at different test conditions (FOL-005, FOL-014, coated or in solution, 48 h incubation) and during the last 20 hours of culture period the cells were pulsed with 1μ Ci/well of [methyl-3H] thymidine. The cells were then harvested onto glass fiber filters using a FilterMate harvester. The filters were air dried, and the bound radioactivity was measured using a liquid scintillation counter. To study whether FOL-005 influenced β-cell proliferation, INS-1 cells were treated with increasing amounts of soluble FOL-005 (0.06-6 μM) during 48 hours and proliferation was measured with radiolabeled thymidine incorporation into newly synthesized DNA. FOL-005 stimulated INS-1 cell proliferation (FIG. 1A). Wells coated with either FOL-005 or FOL-014 and later blocked with bovine serum albumin (BSA) before addition of INS-1 cells also stimulated proliferation compared to control (ctrl) coated wells (FIG. 1B-C).

This demonstrated that FOL-005 and FOL-014 interacted with β-cells and induced proliferation.

Example 3: FOL-005 Protected β-Cells from Glucotoxicity

Since glucotoxicity in pancreatic β-cells is a well-established process in type 2 diabetes we next investigated the protective effects of FOL-005 on β-cells during glucotoxic conditions. First we confirmed that 20 mM glucose induced cell apoptosis in INS cells after 48 h of exposure. High glucose (20 mM) containing RPMI medium induced more Annexin V positive cells and more caspase-3 activity in INS cells compared to cells incubated with medium containing 5 mM glucose (FIG. 2A-B). Exposure of INS-1 cells to 20 mM of glucose at the same time as FOL-005 decreased cell apoptosis as detected both by Annexin V staining and by caspase-3 activity (FIG. 2 A-B). The rate of apoptosis in INS-1 cells was measured with either Caspase-3 Assay Kit or stained with Annexin V Apoptosis Detection Kit with 7-AAD. Caspase-3 activity was measured with fluorescence at an excitation wavelength of 380 nm and an emission wavelength of 440 nm. Caspase-3 activity was then normalized to protein concentration in each well. Measurements of Annexin V stained cells were performed using a CyAn ADP flow cytometer and analyzed with Summit V4.3 software.

In conclusion, it is well known that glucotoxicity induces β-cell apoptosis, however in the presence of FOL-005 glucotoxicity-induced apoptosis was diminished.

Example 4: FOL-005 Induced Insulin Secretion from INS-1 Cells

To investigate the stimulatory effect of FOL-005 on insulin secretion, INS-1 β-cells were used in the following experiments. Cells were seeded overnight in cRPMI and then washed with PBS before pre-incubation for 60 min at 37° C. in Krebs-Ringer bicarbonate buffer (KRB), pH 7.4, supplemented with 10 mM HEPES, 0.1% bovine serum albumin. After pre-incubation, the buffer was changed and the INS-1 cells were incubated at different test conditions (0 mM, 5 mM or 20 mM glucose) and stimulated with peptide FOL-005 or FOL-015 (SEQ ID NO: 158) or left untreated during 60 min at 37° C. Immediately after incubation, an aliquot of the buffer was removed and frozen for subsequent assay of insulin with an insulin radioimmunoassay kit.

The results demonstrated that β-cells stimulated with FOL-005 peptide secreted more insulin compared to unstimulated control cells or to cells stimulated with the FOL-015 control peptide (FIG. 3A) under conditions without glucose. INS-1 β-cells subjected to glucose (5 mM or 20 mM) responded with insulin secretion after FOL-005 peptide (6 μM) stimulation (FIG. 3B). INS-1 cells stimulated with 6 μM FOL-005 peptide in the presence of 20 mM glucose responded with more insulin secretion compared to FOL-005 stimulated cells incubated with 5 mM glucose (FIG. 3B).

Example 5: FOL-005 Induced Insulin Secretion from Mouse Pancreatic Islets

Mouse pancreatic islets were isolated from 8-week old C57BL/6J male mice (Taconic). Mice were sacrificed by an overdose of isoflurane and cervical dislocation. 3 ml of 0.9 U/ml collagenase P was injected into the pancreatic duct to inflate the pancreas. The pancreas was then removed and collagen digested for 19 min at 37° C. The samples were vigorously shaken to disrupt the tissue. The digest was transferred into ice cold Hank's Balanced Salt Solution (HBSS) with $Ca^{2+}$ and $Mg^{2+}$. The suspension was allowed to sit for 10 min to allow the islet to sink, and the islets were washed in fresh HBSS four times. The islets were then hand-picked and sorted according to size. Islets (n=3 per well in a 96 well plate) were pre-incubated in KRB buffer during 10 min 37° C., pH 7.4, supplemented with 10 mM HEPES, 0.1% bovine serum albumin. After pre-incubation, the buffer was changed and islets were incubated at different test conditions in new KRB buffer with 0.1% bovine serum albumin (non-treated ctrl, FOL-005 peptide, or GLP-1) for 60 min at 37° C. Immediately after incubation, an aliquot of the buffer was removed and frozen for subsequent assay of insulin.

The results demonstrated that isolated mouse pancreatic islets stimulated with GLP-1 (100 nM) or FOL-005 (6 μM) secreted more insulin compared to unstimulated control islets (FIG. 3C).

Example 6: FOL-014 Induced Insulin Secretion from INS-1 Cells

INS-1 β-cells were used to investigate the stimulatory effect of FOL-014 on insulin secretion. Cells were seeded overnight and then washed with PBS before pre-incubation for 60 min at 37° C. in Krebs-Ringer bicarbonate buffer (KRB), pH 7.4, supplemented with 10 mM HEPES, 0.1% bovine serum albumin. After pre-incubation, the buffer was changed and the INS-1 cells were incubated in new KRB buffer supplemented with 10 mM HEPES, 0.1% bovine serum albumin and stimulated with peptide FOL-014 or left untreated during 60 min at 37° C. Immediately after incubation, an aliquot of the buffer was removed and frozen for subsequent assay of insulin.

The results demonstrated that β-cells stimulated with FOL-014 peptide secreted more insulin compared to unstimulated control cells (FIG. 4A).

Example 7: FOL-014 Induced Insulin Secretion from Mouse Pancreatic Islets

Mouse pancreatic islets were isolated from 8-week old C57BL/6J male mice as described under example 5. The islets were then hand-picked and sorted according to size. Islets (n=5 per well in a 96 well plate) were pre-incubated in 200 μl KRB buffer during 10 min 37° C., pH 7.4, supplemented with 10 mM HEPES, 0.1% bovine serum albumin. Following pre-incubation, the buffer was changed and islets were incubated in different test conditions in new KRB buffer with 0.1% bovine serum albumin (non-treated ctrl, FOL-014 peptide, and GLP-1) for 60 min at 37° C. Immediately after incubation, an aliquot of the buffer was removed and frozen for subsequent assay of insulin.

The result show that mouse pancreatic islets stimulated with FOL-014 (6 μM) secreted more insulin compared to unstimulated control islets (FIG. 4B). GLP-1 (100 nM) or FOL-014 (0.6 μM) did not affect insulin secretion (FIG. 4B).

Example 8-11: Stimulation of Insulin Secretion from INS-1 Cell Ones by FOL-014, FOL-005 and Related Peptides Materials and methods: Rat INS-1 β-cells (passages 60-70) were cultured at 37° C. and 5% $CO_2$ in cRPMI media (RPMI 1640 supplemented with 10% fetal bovine serum, 50 IU/mL penicillin, 50 mg/L streptomycin, 10 mM HEPES, 2 mM L-glutamine, 1 mM sodium pyruvate, and 50 μM beta-mercaptoethanol) unless otherwise stated. INS-1 cells were seeded in 96-well plates ($2 \times 10^3$ cells/well) in cRPMI medium and following overnight incubation, the cells were washed in PBS before pre-incubation for 120 min at 37° C. in Krebs-Ringer bicarbonate buffer, pH 7.4, supplemented with 10 mM HEPES, 0.1% bovine serum albumin and 2.8 mM glucose. Following pre-incubation, the buffer was exchanged with fresh Krebs-Ringer buffer as described above and supplemented with specific glucose concentrations and peptides for the individual experiments as described below. Immediately after 60 minutes incubation at 37° C., an aliquot of the buffer was removed and frozen for subsequent insulin ELIZA assay.

Example 8. FOL-014 Induced Insulin Secretion is Dose-Dependent in a Non-Linear Manner Insulin release from INS-1 cells were measured following exposure to increasing concentrations of FOL-014 and compared with the stimulatory effect of GLP-1 and untreated control during high glucose concentration (16.7 mM). All concentrations of FOL-014 tested elicited significantly higher insulin release as compared with the untreated control. At 6 nM or higher, FOL-014 triggered insulin release within the same range as 100 mM GLP-1. At concentrations ranging from 0.6-60 nM, insulin secretion increased in a linear fashion in relation to increasing FOL-014 concentrations. Exposure to FOL-014 concentrations 600 nM did not increase the insulin secretion (FIG. 5).

The results demonstrated that FOL-014 significantly increased insulin secretion from INS-1 β-cells in vitro in a non-linear dose dependent fashion.

Example 9. The Capacity of FOL-014 to Induce Insulin Secretion is Glucose Dependent Insulin release from INS-1 cells was measured following exposure to 60 nM FOL-014 at increasing concentrations of glucose. In untreated control samples, elevated glucose concentrations increased the insulin secretion at 11.1 mM glucose or higher. In the presence of FOL-014, insulin secretion increased significantly in a glucose dependent fashion already from 5.5 mM glucose. (FIG. 6).

The results demonstrated that the presence of FOL-014 significantly increased insulin secretion from INS-1 β-cells in vitro in a glucose concentration dependent fashion and that FOL-014 was effective also at marginally elevated glucose levels.

Example 10. FOL-014 or FOL-005 in Combination with GLP-1 Increased Insulin Secretion as Compared with Either Peptide Alone Insulin secretion from INS-1 cells was measured following exposure to FOL-005, FOL-014, GLP-1 or combinations of those, expressed as percentage of untreated control. The combined effect of GLP-1 and FOL-014 resulted in a significantly higher insulin release than GLP-1 or FOL-014 alone. The additive effect of the combination of FOL-005 and GLP-1 was less pronounced, but did however increase the insulin secretion as compared with GLP-1 alone. The experiments were performed in the presence of 16.7 mM glucose (FIG. 7).

The results demonstrated that the combination of GLP-1 and FOL-014 could further potentiate the insulin secretion from INS-1 cells in vitro as compared with each peptide alone. Furthermore, the combination of FOL-005 and GLP-1 tendentially increased insulin secretion.

Example 11. The Ability of Novel Peptide Analogues to Induce Insulin Secretion in Pancreatic β-Cell-Lines was Investigated Novel peptide analogues, derived from either FOL-005 or FOL-014 were tested concerning their ability to induce insulin secretion in two separate INS-1 cell lines in the presence of 16.7 mM glucose. FOL-005, FOL-014 and GLP-1 as well as a high glucose (16.7 mM) and a low glucose (2.8 mM) control (not shown) was included in each experiment and the peptide concentration was 100 nM. In order to correct for the variance between experiments, all values were normalized to, and expressed as percentage of the average value of the high glucose control in the individual experiments. The analogues were subsequently ranked according to performance (FIGS. 11A and 11B). Peptide analogues eliciting an insulin response below the high glucose control average value were considered non-functional and were hence excluded (not shown).

The results demonstrated the capacity of several novel peptide analogues to enhance insulin secretion from INS-1 β-cells in vitro.

Example 12. FOL-014 Increase Insulin Secretion from Mouse-Derived Pancreatic Islets Twelve-week-old male C57/bl6 mice were euthanized with isoflurane and cervical dislocation. After clamping the hepatic ducts, 3 ml of 0.9 U/ml collagenase P was injected into the bile duct to inflate the pancreas. The pancreas was then removed and digested for 19 min at 37° C. The samples were vigorously shaken to disrupt the tissue. The digest was quickly transferred into ice cold Hank's Balanced Salts Solution with $Ca^{2+}$ and $Mg^{2+}$. The suspension was allowed to sit for 8 min to allow the islet to sink, and the islets were washed in the same manner four times. The islets were then handpicked and sorted according to size.

Freshly isolated islets were seeded in groups of 5 in a 96-well plate and preincubated for 1 h at 37° C. in a Krebs-Ringer bicarbonate buffer (pH 7.4). The islets were incubated for 1 h at 37° C. in Krebs-Ringer buffered solution supplemented with 0.6 or 6 µM FOL-014 or 100 nM GLP-1 or left unsupplemented for control. Immediately after incubation, the medium was removed for assays of insulin and glucagon using Mercodia's ELISA kits. The effect of FOL-014 on insulin (FIGS. 8A and B) and glucagon (FIGS. 8C and D) secretion from isolated mouse islets was measured in the presence of low glucose (2.8 mM; FIGS. 8A and C) or high glucose (16.7 mM; FIGS. 8B and D) concentrations. A significant effect of FOL-014 was observed in the presence of high glucose for insulin and in the presence of both high and low glucose for glucagon. The effect of FOL-014 differed from that of GLP-1, which enhanced insulin secretion also in low glucose samples but failed to inhibit glucagon secretion in low glucose conditions.

The results demonstrated that FOL-014 enhanced insulin secretion and inhibited glucagon secretion in pancreatic islets.

Example 13. FOL-014 Reduced Plasma Glucose Levels in an Intraperitoneal Glucose Tolerance Test (IPGTT) in Mice Whole blood was collected for glucose and insulin measurements from 10-week-old wild type male C57bl/6 mice. After a 4 hour fast, the mice were divided into three groups and given an intraperitoneal injection (ip) of either saline, 30 nmol/kg peptide (FIG. 9A) or 200 nmol/kg peptide (FIG. 9B). 15 min after the FOL-014 or saline (control) injections, the mice were administered 2 g of glucose/kg ip. Blood glucose concentrations were measured at 5, 15, 30, 45 and 60 minutes after the glucose injection. Statistical calculations were performed using student's t-test. FOL-014 dosed at 200 nmol/kg significantly lowered the plasma glucose levels as compared to the control when measured as area under the curve. In addition, the difference was significant at 15, 30 and 45 minutes. At the 30 nmol/kg dose, FOL-014 lowered the plasma glucose levels with a significant effect at 45 minutes after the glucose injection.

The results demonstrated that FOL-014 could lower plasma glucose levels in a glucose tolerance test performed on healthy wild type mice.

Example 14. FOL-014 Delayed Onset of Type 1 Diabetes in BB Lyp/Lyp Rats

BB lyp/lyp rats were randomized for placebo (sodium chloride, 9 mg/ml) or FOL-014 treatment 3 times/week from day 40 until onset of type 1 diabetes, defined as plasma glucose levels 11.1 mM. The dose of 100 nmol/kg FOL-014 peptide in saline or placebo (saline) was administered subcutaneously and the animals were terminated immediately upon exceeding critical plasma glucose levels. The difference between FOL-014 treated animals and animals receiving placebo treatment was significant both when expressed as average age for onset of type 1 diabetes (FIG. 10A) and when described as percentage of animals developing type 1 diabetes per day (FIG. 10B).

The results demonstrated that FOL-014 treatment significantly delayed the onset of type-1 diabetes in BB lyp/lyp rats.

Example 15. FOL-005 and FOL-014 Displayed Organ Specific Distribution Patterns in Mice C57Bl/6 mice were injected subcutaneously with $H^3$ labelled FOL-005 and euthanized at 1 h (FIG. 12A) or 2 h (FIG. 12B) after injection. Following whole body sectioning the distribution of the labelled peptide was visualised. Strong binding was evident in pancreas and at the site of injection. Using Pearl Trilogy Small Animal Imaging System, in vivo bio-distribution and tissue localization of two Cy7.5 labelled peptides, FOL-005 (FIG. 12C) and FOL-014 (FIG. 12D) in NMRI nude mice via subcutaneous injection was investigated. High accumulation of the peptide was evident in the pancreatic tissue area. The same distribution pattern was found after i.v. administrations (not shown). The dose of each peptide was 10 nmol per mouse. The mice were imaged before injection, at 5 min, 20 min, 50 min, 60 min, 2 hrs, 4 hrs, 6 hrs, 24 hrs and 48 hrs post administration of labelled peptide.

Example 16. Tissue Specific Imaging for Diagnostic Use

Agents prepared as defined herein above are labelled by conjugation to suitable imaging probe or moiety, using methods known by those of skill in the art. The conjugated peptide-probe agents are subsequently administered to a subject and biodistribution is subsequently monitored e.g. up to 48 h after administration. The conjugated agent is thus used as a diagnostic or prognostic tool for investigation of pancreatic status. As such, the conjugated agents are suitable for detecting, diagnosing, or monitoring disease, disease processes and progression, susceptibility, as well as to determine efficacy of a treatment. The agents are particularly suited for monitoring the diabetic status of a subject. The conjugated agents are also used for monitoring and/or predicting risk of developing a disease, specifically diabetes. The test is used alone or in combination with other tests known by those of skill in the art, such as blood tests, genetic testing, urine test, and biopsies.

Example 17: Sequence Overview

| SEQ ID NO | Sequence | Notes |
|---|---|---|
| 1 | VDTYDGDISVVYGLR | FOL-005 |
| 2 | VDTYDGDISVVYGLS | |
| 3 | VDTYDGDISVVYGL | FOL-025 |
| 4 | DTYDGDISVVYGLR | |
| 5 | TYDGDISVVYGLRS | |
| 6 | VDTYDGDISVVYG | FOL-024 |
| 7 | DTYDGDISVVYGL | |
| 8 | TYDGDISVVYGLR | |
| 9 | YDGDISVVYGLRS | |
| 10 | VDTYDGDISVVY | |
| 11 | DTYDGDISVVYG | |
| 12 | TYDGDISVVYGL | |
| 13 | YDGDISVVYGLR | |
| 14 | DGDISVVYGLRS | |
| 15 | VDTYDGDISVV | |
| 16 | DTYDGDISVVY | |
| 17 | TYDGDISVVYG | |
| 18 | YDGDISVVYGL | |
| 19 | DGDISVVYGLR | |
| 20 | GDISVVYGLRS | |
| 21 | VDTYDGDISV | |
| 22 | DTYDGDISVV | |
| 23 | TYDGDISVVY | |
| 24 | YDGDISVVYG | |
| 25 | DGDISVVYGL | |
| 26 | GDISVVYGLR | FOL-009h |
| 27 | DISVVYGLRS | |
| 28 | VDTYDGDIS | FOL-019h |
| 29 | DTYDGDISV | |
| 30 | TYDGDISVV | |
| 31 | YDGDISVVY | |
| 32 | DGDISVVYG | |
| 33 | GDISVVYGL | |
| 34 | DISVVYGLR | |
| 35 | ISVVYGLRS | |
| 36 | VDTYDGDI | |
| 37 | DTYDGDIS | |
| 38 | TYDGDISV | |
| 39 | YDGDISVV | |
| 40 | DGDISVVY | |
| 41 | GDISVVYG | |
| 42 | DISVVYGL | |
| 43 | ISVVYGLR | |
| 44 | VDTYDGD | |
| 45 | DTYDGDI | |
| 46 | TYDGDIS | |
| 47 | YDGDISV | |
| 48 | DGDISVV | |
| 49 | GDISVVY | |
| 50 | DISVVYG | |
| 51 | ISVVYGL | |
| 52 | DTYDGD | |
| 53 | TYDGDI | |
| 54 | YDGDIS | |
| 55 | DGDISV | |
| 56 | GDISVV | |
| 57 | DISVVY | |
| 58 | ISVVYG | |
| 59 | TYDGD | |
| 60 | YDGDI | |
| 61 | DGDIS | |
| 62 | GDISV | |
| 63 | DISVV | |
| 64 | ISVVY | |
| 65 | SVVYG | |
| 66 | MRIAVICFCLLGITCAIPVKQADSGSSEEKQLYNKYPDAVATWLNPDPSQKQNLLAPQTLPSKSNESHDHMDDMDDEDDDDHVDSQDSIDSNDSDDVDDTDDSHQSDESHHSDESDELVTDFPTDLPATEVFTPVVPT*VDTYDGRGDSVVYGLRS*KSKKFRRPDIQYPDATDEDITSHMESEELNGAYKAIPVAQDLNAPSDWDSRGKDSYETSQLDDQSAETHSHKQSRLYKRKANDESNEHSDVIDSQELSKVSREFHSHEFHSHEDMLVVDPKSKEEDKHLKFRISHELDSASSEVN | Wildtype human osteopontin, i.e. GenBank: AAA59974.1 |
| 67 | VDTYDGRGDSVVYGLR | FOL-002 |
| 68 | VDZ$_3$Z$_4$Z$_5$GZ$_7$Z$_8$SZ$_{10}$Z$_{11}$YGLR | Z$_3$ is T or V; |

-continued

| SEQ ID NO | Sequence | Notes |
|---|---|---|
| | | $Z_4$ is Y or P; $Z_5$ is D or N; $Z_7$ is D or G; $Z_8$ is I or G; $Z_{10}$ is V or L; $Z_{11}$ is V or A |
| 69 | VDVPNGDISLAYGLR | FOL-004 |
| 70 | DVPNGDISLAYGLRS | |
| 71 | VDVPNGDISLAYGL | FOL-016 |
| 72 | DVPNGDISLAYGLR | FOL-007 |
| 73 | VPNGDISLAYGLRS | |
| 74 | VDVPNGDISLAYG | FOL-017 |
| 75 | DVPNGDISLAYGL | |
| 76 | VPNGDISLAYGLR | |
| 77 | PNGDISLAYGLRS | |
| 78 | VDVPNGDISLAY | |
| 79 | DVPNGDISLAYG | |
| 80 | VPNGDISLAYGL | |
| 81 | PNGDISLAYGLR | FOL-008 |
| 82 | NGDISLAYGLRS | |
| 83 | VDVPNGDISLA | FOL-018 |
| 84 | DVPNGDISLAY | |
| 85 | VPNGDISLAYG | |
| 86 | PNGDISLAYGL | |
| 87 | NGDISLAYGLR | |
| 88 | GDISLAYGLRS | |
| 89 | VDVPNGDISL | |
| 90 | DVPNGDISLA | |
| 91 | VPNGDISLAY | |
| 92 | PNGDISLAYG | |
| 93 | NGDISLAYGL | |
| 94 | GDISLAYGLR | FOL-009 |
| 95 | DISLAYGLRS | |
| 96 | VDVPNGDIS | FOL-019 |
| 97 | DVPNGDISL | |

-continued

| SEQ ID NO | Sequence | Notes |
|---|---|---|
| 98 | VPNGDISLA | |
| 99 | PNGDISLAY | |
| 100 | NGDISLAYG | |
| 101 | GDISLAYGL | |
| 102 | DISLAYGLR | |
| 103 | ISLAYGLRS | |
| 104 | VDVPNGDI | |
| 105 | DVPNGDIS | |
| 106 | VPNGDISL | |
| 107 | PNGDISLA | |
| 108 | NGDISLAY | |
| 109 | GDISLAYG | |
| 110 | DISLAYGL | |
| 111 | ISLAYGLR | |
| 112 | VDVPNGD | |
| 113 | DVPNGDI | |
| 114 | VPNGDIS | |
| 115 | PNGDISL | |
| 116 | NGDISLA | |
| 117 | GDISLAY | |
| 118 | DISLAYG | |
| 119 | ISLAYGL | |
| 120 | DVPNGD | |
| 121 | VPNGDI | |
| 122 | PNGDIS | |
| 123 | NGDISL | |
| 124 | GDISLA | |
| 125 | DISLAY | |
| 126 | ISLAYG | |
| 127 | VPNGD | |
| 128 | PNGDI | |
| 129 | NGDIS | |
| 130 | GDISL | |
| 131 | DISLA | |
| 132 | ISLAY | |
| 133 | SLAYG | |

| SEQ ID NO | Sequence | Notes |
|---|---|---|
| 134 | MRLAVICFCLFGIASSLPVKVTDSGSSEEKLYSLHPDPIATWLVPDPSQKQNLLAPQNAVSSEEKDDFKQETLPSNSNESHDHMDDDDDDDDDGDHAESEDSVDSDSDESHHSDSDETVTASTQADTFTPIVPT*VDVPNGRGDSLAYGLR*SKSRSFQVSDEQYPDATDEDLTSHMKSGESKESLDVIPVAQLLSMPSDQDNNGKGSHESSQLDEPSLETHRLEHSKESQESADQSDVIDSQASSKASLEHQSHKFHSHKDKLVLDPKSKEDDRYLKFRISHELESSSSEVN | Wildtype murine osteopontin, i.e. NCBI Reference Sequence: NP_001191162.1 |
| 135 | VDVPNGRGDSLAYGLR | FOL-001 |
| 136 | KPLAEIDSIELSYGIK | FOL-014 |
| 137 | GDPNDGRGDSVVYGLR | FOL-003 |
| 138 | VDTYDGGISVVYGLR | FOL-026 |
| 139 | VDTYDGDSVVYGLR | FOL-027 |
| 140 | $KX_2LAX_5X_6X_7X_8IX_{10}LX_{12}YGIK$ | $X_2$ is C, P or G; $X_5$ is E or G; $X_6$ is C, D or I; $X_7$ is D, I, S or G; $X_8$ is S, D or G; $X_{10}$ is E or G; $X_{12}$ is S or T; |
| 141 | KCLAECDSIELSYGIK (Cyclic) | FOL-032 |
| 142 | CLAEIDSC (Cyclic) | FOL-033 |
| 143 | CFKPLAEIDSIECSYGIK (Cyclic) | FOL-036 |
| 144 | KPLAEDISIELSYGIK | FOL-037 |
| 145 | KPLAEISDIELSYGIK | FOL-038 |
| 146 | KPLAEIGDIELSYGIK | FOL-039 |
| 147 | KPLAEGDIELSYGIK | FOL-040 |
| 148 | KPLAEIELSYGIK | FOL-041 |
| 149 | KPLAEIDSIELTYGIK | FOL-042 |
| 150 | KPLAEIDGIELSYGIK | FOL-043 |
| 151 | KPLAEIDGIELTYGIK | FOL-044 |
| 152 | KPLAEIGSIELSYGIK | FOL-045 |
| 153 | KGLAEIDSIELSYGIK | FOL-046 |
| 154 | KPLAGIDSIGLSYGIK | FOL-047 |
| 155 | Cyclic KCLAEIDSCELSYGIK | FOL-034 |
| 156 | Cyclic CFKPLAEIDSIEC | FOL-035 |
| 157 | VDVPEGDISLAYGLR | FOL-010 |
| 158 | LDGLVRAYDNISPVG | FOL-015 |
| 159 | GDPNGDISVVYGLR | FOL-006 |
| 160 | VDVPNGDISLAYRLR | FOL-011 |
| 161 | VDVPEGDISLAYRLR | FOL-012 |
| 162 | $KX_2LAX_5X_6X_7X_8IX_{10}LSYGIK$ | $X_2$ is C, P or G; $X_5$ is E or G; $X_6$ is C, I or absent; $X_7$ is D, G or absent; $X_8$ is S, G or absent; $X_{10}$ is E or G; |
| 163 | $KX_2LAX_5IX_{10}LSYGIK$ | $X_2$ is C, P or G; $X_5$ is E or G; $X_{10}$ is E or G. |
| 164 | $VDVPZ_5GDISLAYZ_{13}LR$ | $Z_5$ is E or N; $Z_{13}$ is R or G. |
| 165 | $VDTYDGZ_7Z_8SVVYGLR$ | $Z_7$ is D or G; $Z_8$ is I or G. |
| 166 | $GDPNZ_5Z_6Z_7Z_8Z_9SVVYGLR$ | $Z_5$ is D or G; $Z_6$ is D or G; $Z_7$ is I or R; $Z_8$ is G or absent; $Z_9$ is D or absent. |
| 167 | $VZ_2TYDGDISVVYGLR$ | $Z_2$ is beta D FOL-005 (2betaAsp) |
| 168 | $VDTY Z_5GDISVVYGLR$ | $Z_5$ is beta D FOL-005 (5betaAsp) |
| 169 | $VDTYDG Z_7ISVVYGLR$ | FOL-005 (7betaAsp) $Z_7$ is beta D |

The invention claimed is:

1. An agent comprising:
   a) a peptide comprising or consisting of the amino acid sequence KCLAECDSIELSYGIK (SEQ ID NO: 141), KPLAEDISIELSYGIK (SEQ ID NO: 145), KPLAEIGDIELSYGIK (SEQ ID NO: 146), KPLAEIGSIELSYGIK (SEQ ID NO: 152), KGLAEIDSIELSYGIK (SEQ ID NO: 153); KPLAGIDSIGLSYGIK (SEQ ID NO: 154), CLAEIDSC (SEQ ID NO: 142), CFKPLAEIDSIECSYGIK (SEQ ID NO: 143), KPLAEGDIELSYGIK (SEQ ID NO: 147), KPLAEIELSYGIK (SEQ ID NO: 148), KCLAEIDSCELSYGIK (SEQ ID NO: 155), CFKPLAEIDSIEC (SEQ ID NO: 156), VDTYDGGISVVYGLR (SEQ ID NO: 138), VDTYDGDGSVVYGLR (SEQ ID NO: 139), VDVPEGDISLAYGLR (SEQ ID NO: 157), LDGLVRAYDNISPVG (SEQ ID NO: 158), GDPNGDISVVYGLR (SEQ ID NO: 159), VDVPNGDISLAYRLR (SEQ ID NO: 160), VDVPEGDISLAYRLR (SEQ ID NO: 161), V(beta-D)TYDGDISVVYGLR (SEQ ID NO:167), VDTY(beta-D)GDISVVYGLR (SEQ ID NO: 168), or VDTYDG(beta-D)ISVVYGLR (SEQ ID NO: 169);
   b) a polynucleotide encoding upon expression, the peptide of a);

c) a vector comprising the polynucleotide of b); or d) a cell comprising the polynucleotide of b), or the vector of c).

2. The agent according to claim 1, wherein the peptide comprises or consists of:

an amino acid sequence selected from the group consisting of KCLAECDSIELSYGIK (SEQ ID NO: 141), KPLAEDISIELSYGIK (SEQ ID NO: 145), KPLAEIGDIELSYGIK (SEQ ID NO: 146), KPLAEIGSIELSYGIK (SEQ ID NO: 152), KGLAEIDSIELSYGIK (SEQ ID NO: 153), KPLAGIDSIGLSYGIK (SEQ ID NO: 154); CLAEIDSC (SEQ ID NO: 142), CFKPLAEIDSIEC-SYGIK (SEQ ID NO: 143), KPLAEGDIELSYGIK (SEQ ID NO: 147), KPLAEIELSYGIK (SEQ ID NO: 148), KCLAEIDSCELSYGIK (SEQ ID NO: 155), and CFKPLAEIDSIEC (SEQ ID NO: 156).

3. The agent according to claim 1, wherein the peptide comprises no more than 85 amino acids.

4. The agent according to claim 1, wherein the peptide comprises at least 2 additional amino acids conjugated to the N- or C-terminus of the peptide.

5. The agent according to claim 1, wherein the agent is conjugated to a moiety.

6. The agent according to claim 1, wherein the peptide is further modified by glycosylation, PEGylation, amidation, esterification, acylation, acetylation and/or alkylation.

7. The agent according to claim 1, wherein the agent comprises or consists of tandem repeats of the peptides of claim 1.

8. The agent according to claim 1, wherein the peptide is fused to another polypeptide.

9. The agent according to claim 8, wherein the another polypeptide is selected from the group consisting of glutathione-S-transferase (GST) and protein A.

10. The agent according to claim 1, wherein the peptide is fused to a tag.

11. The agent according to claim 1, wherein the peptide is cyclic.

12. The agent according to claim 1, wherein the peptide comprises or consists of one or more additional amino acids inserted at the N- and/or C-terminus.

13. The agent according to claim 1, wherein the agent further comprises a detectable moiety.

14. The agent according to claim 1, wherein the agent comprises:
   a) a peptide
      comprising or consisting of the amino acid sequence VDTYDGGISVVYGLR (SEQ ID NO: 138), VDTYDGDGSVVYGLR (SEQ ID NO: 139), VDVPEGDISLAYGLR (SEQ ID NO: 157), LDGLVRAYDNISPVG (SEQ ID NO: 158), GDPNGDISVVYGLR (SEQ ID NO: 159), VDVPNGDISLAYRLR (SEQ ID NO: 160) VDVPEGDISLAYRLR (SEQ ID NO: 161), V(beta-D)TYDGDISVVYGLR (SEQ ID NO:167), VDTY(beta-D)GDISVVYGLR (SEQ ID NO: 168), or VDTYDG(beta-D)ISVVYGLR (SEQ ID NO:169);
   b) a polynucleotide encoding upon expression, the peptide of a);
   c) a vector comprising the polynucleotide of b); or
   d) a cell comprising the polynucleotide of b), or the vector of c).

15. The agent according to claim 14, wherein the peptide comprises or consists of the amino acid sequence VDTYDGGISVVYGLR (SEQ ID NO: 138).

16. A method of treating diabetes and/or a diabetes associated disorder or disease, the method comprising administering to a subject in need thereof a therapeutically effective amount of an agent comprising:
   a peptide comprising or consisting of an amino acid sequence selected from the group consisting of VDTYDGGISVVYGLR (SEQ ID NO: 138), CLAEIDSC (SEQ ID NO: 142), CFKPLAEIDSIECSYGIK (SEQ ID NO: 143), KPLAEGDIELSYGIK (SEQ ID NO: 147), KPLAEIELSYGIK (SEQ ID NO: 148), KCLAEIDSCELSYGIK (SEQ ID NO: 155), CFKPLAEIDSIEC (SEQ ID NO: 156), KCLAECDSIELSYGIK (SEQ ID NO: 141), KPLAEDISIELSYGIK (SEQ ID NO: 145), KPLAEIGDIELSYGIK (SEQ ID NO: 146), KPLAEIGSIELSYGIK (SEQ ID NO: 152), KGLAEIDSIELSYGIK (SEQ ID NO: 153), and KPLAGIDSIGLSYGIK (SEQ ID NO: 154).

17. The method according claim 16, wherein said agent comprises a second or further active ingredient.

18. The method according to claim 17, wherein the second or further active ingredient is selected from the group consisting of insulin, glucagon-like peptide-1 (GLP-1), sulfonylurea, a dipeptidyl peptidase-4 (DPP4) inhibitor, an alpha-glucosidase inhibitor, a thiazolidinedione, a meglitidine and a sodium-glucose cotransporter-2 (SGLT2) inhibitor.

19. The method according to claim 16, wherein the diabetes and/or a diabetes associated disorder or disease is selected from the group consisting of diabetes mellitus, type 1 diabetes mellitus, type 2 diabetes mellitus, malnutrition-related diabetes mellitus, disorders of glucose regulation and pancreatic internal secretion, insulin resistance syndrome, impaired glucose tolerance, hyperglycemia, hyperinsulinemia, and any combinations thereof.

20. The method according to claim 16, wherein the diabetes and/or a diabetes associated disorder or disease is diabetes mellitus selected from the group consisting of type 1 diabetes mellitus, type 2 diabetes mellitus, malnutrition-related diabetes mellitus, specified diabetes mellitus, and unspecified diabetes mellitus.

21. The method according to claim 16, wherein the peptide comprises or consists of an amino acid sequence selected from the group consisting of KCLAECDSIELSYGIK (SEQ ID NO: 141), KPLAEDISIELSYGIK (SEQ ID NO: 145), KPLAEIGDIELSYGIK (SEQ ID NO: 146), KPLAEIGSIELSYGIK (SEQ ID NO: 152), KGLAEIDSIELSYGIK (SEQ ID NO: 153), and KPLAGIDSIGLSYGIK (SEQ ID NO: 154).

22. A method for delaying onset of diabetes and/or a diabetes associated disorder or disease, the method comprising administering a therapeutically effective amount of an agent to an individual in need thereof,
   wherein the agent comprises or consists of the amino acid sequence KCLAECDSIELSYGIK (SEQ ID NO: 141), KPLAEDISIELSYGIK (SEQ ID NO: 145), KPLAEIGDIELSYGIK (SEQ ID NO: 146), KPLAEIGSIELSYGIK (SEQ ID NO: 152), KGLAEIDSIELSYGIK (SEQ ID NO: 153); KPLAGIDSIGLSYGIK (SEQ ID NO: 154); CLAEIDSC (SEQ ID NO: 142), CFKPLAEIDSIECSYGIK (SEQ ID NO: 143), KPLAEGDIELSYGIK (SEQ ID NO: 147), KPLAEIELSYGIK (SEQ ID NO: 148), KCLAEIDSCELSYGIK (SEQ ID NO: 155), CFKPLAEIDSIEC (SEQ ID NO: 156), VDTYDGGISVVYGLR (SEQ ID NO: 138), VDTYDGDGSWYGLR (SEQ ID NO: 139), VDVPEGDISLAYGLR (SEQ ID NO: 157), LDGLVRAYDNISPVG (SEq ID NO: 158), GDPNGDISVVYGLR (SEQ ID NO: 159), VDVPNGDISLAYRLR (SEq ID NO: 160), VDVPEGDISLAYRLR (SEQ ID NO: 161), V(beta-D)TYDGDISVVYGLR (SEQ ID NO: 167), VDTY(beta-D)GDISVVYGLR (SEQ ID NO: 168), or VDTYDG(beta-D)ISVVYGLR (SEQ ID NO: 169).

23. The method according to claim 22, wherein insulin secretion is increased.

24. The method according to claim 22, wherein cellular uptake of glucose is increased.

* * * * *